(12) United States Patent
Sedelmeier et al.

(10) Patent No.: US 7,772,405 B2
(45) Date of Patent: Aug. 10, 2010

(54) 3-ALKYL-5-(4-ALKYL-5-OXO-TETRAHYDROFUTRAN-2-YL) PYRROLIDIN-2-ONE DERIVATIVES AS INTERMEDIATES IN THE SYNTHESIS OF RENIN INHIBITORS

(75) Inventors: Gottfried Sedelmeier, Schallstadt (DE); Dominique Grimler, Hirsingue (FR); Murat Acemoglu, Basel (CH)

(73) Assignee: Novartis AG, Basel (CH)

( * ) Notice: Subject to any disclaimer, the term of this patent is extended or adjusted under 35 U.S.C. 154(b) by 195 days.

(21) Appl. No.: 12/088,457

(22) PCT Filed: Oct. 16, 2006

(86) PCT No.: PCT/EP2006/009970

§ 371 (c)(1),
(2), (4) Date: Apr. 15, 2008

(87) PCT Pub. No.: WO2007/045420

PCT Pub. Date: Apr. 26, 2007

(65) Prior Publication Data

US 2008/0262246 A1    Oct. 23, 2008

(30) Foreign Application Priority Data

Oct. 17, 2005    (GB) .................................. 0521083.6

(51) Int. Cl.
C07D 405/04 (2006.01)
(52) U.S. Cl. .................................................. 548/517
(58) Field of Classification Search .................. 548/517
See application file for complete search history.

(56) References Cited

U.S. PATENT DOCUMENTS

| | | | |
|---|---|---|---|
| 5,559,111 A | 9/1996 | Goeschke et al. | 514/227 |
| 5,606,078 A | 2/1997 | Goeschke et al. | 549/321 |
| 5,627,182 A | 5/1997 | Goeschke et al. | 514/237.8 |
| 5,646,143 A | 7/1997 | Goeschke et al. | 514/233.8 |
| 5,654,445 A | 8/1997 | Goeschke et al. | 549/321 |
| 5,659,065 A | 8/1997 | Goeschke et al. | 560/29 |
| 5,705,658 A | 1/1998 | Goeschke et al. | 549/321 |

FOREIGN PATENT DOCUMENTS

| EP | 0 678 503 | 9/1999 |
|---|---|---|
| WO | WO2005/051895 | 6/2005 |
| WO | WO2006/024501 | 3/2006 |
| WO | WO2006/131304 | 12/2006 |

OTHER PUBLICATIONS

Dong et al., "Practical synthesis of an orally active renin inhibitor aliskiren", Tetrahedron Letters, 46, pp. 6337-6340 (2005).
Mealy et al., "Aliskiren Fumarate", Drugs of the Future, 26 (12): pp. 1139-1148.
Hanessian et al., "The power of visual imagery in synthesis planning. Stereocontrolled approaches to CGP-60536B, a potent renin inhibitor", J. Org. Chem., 67, pp. 4261-4274 (2002).

Primary Examiner—Kamal A Saeed
Assistant Examiner—Samantha L Shterengarts
(74) Attorney, Agent, or Firm—Lisa M. Matovcik

(57) ABSTRACT

The invention related to a novel process, novel process steps and novel intermediates useful in the synthesis of pharmaceutically active compounds, especially renin inhibitors, such as Aliskiren. Inter alia, the invention relates to a process for the manufacture of a compound of the formula II,

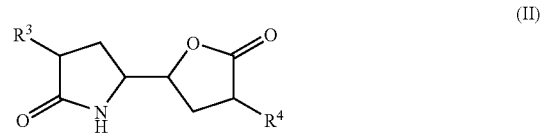

(II)

or a salt thereof, and a compound of formula VI

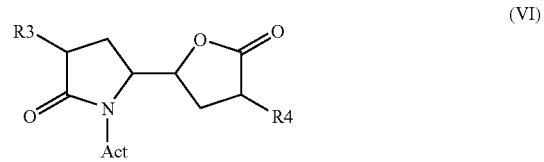

(VI)

or a salt thereof, wherein $R^3$ and $R^4$ as well as Act are as defined in the specification, and processes of manufacturing these.

Additionally transformation of compounds (VI) with metallo organic compounds (VII) give rise to the new compounds (VIII) which are direct precursors for the preparation of Aliskiren.

16 Claims, No Drawings

3-ALKYL-5-(4-ALKYL-5-OXO-TETRAHYDROFUTRAN-2-YL)PYRROLIDIN-2-ONE DERIVATIVES AS INTERMEDIATES IN THE SYNTHESIS OF RENIN INHIBITORS

FIELD OF THE INVENTION

The present invention relates to novel C-8 lactam lactone compounds. Moreover, the present invention provides methods for preparing these C-8 lactam lactone compounds.

These C-8 lactam lactone compounds are more specifically 5-(5-oxo-tetrahydro-furan-2-yl)pyrrolidin-2-one compounds according to formula (II) as shown below. Such compounds are key intermediates in the preparation of renin inhibitors, in particular 2(S),4(S),5(S),7(S)-2,7-dialkyl-4-hydroxy-5-amino-8-aryl-octanoyl amide derivatives, or pharmaceutically acceptable salts thereof. Therefore, present invention is also directed to useful intermediates in the preparation of these renin inhibitors as well as methods for preparing these renin inhibitors and its intermediates.

BACKGROUND OF THE INVENTION

Renin passes from the kidneys into the blood where it affects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is a direct cause of the hypotensive effect of renin inhibitors.

With compounds such as (with INN name) aliskiren ((2S, 4S,5S,7S)-5-amino-N-(2-carbamoyl-2-methylpropyl)-4-hydroxy-2-isopropyl-7-[4-methoxy-3-(3-methoxypropoxy)benzyl]-8-methyl-nonanamide), a new antihypertensive has been developed which interferes with the renin-angiotensin system at the beginning of angiotensin II biosynthesis.

As the compound comprises 4 chiral carbon atoms, the synthesis of the enantiomerically pure compound is quite demanding. Therefore, amended routes of synthesis that allow for more convenient synthesis of this sophisticated type of molecules are welcome.

Such 2(S),4(S),5(S),7(S)-2,7-dialkyl-4-hydroxy-5-amino-8-aryl-octanoyl amide derivatives are any of those having renin inhibitory activity and, therefore, pharmaceutical utility and include, e.g., those disclosed in U.S. Pat. No. 5,559,111. So far, various methods of preparing 2(S),4(S),5(S),7(S)-2,7-dialkyl-4-hydroxy-5-amino-8-aryl-octanoyl amide derivatives are described in the literature.

In EP-A-0678 503, δ-amino-γ-hydroxy-ω-aryl-alkanecarboxamides are described, which exhibit renin-inhibiting properties and could be used as antihypertensive agents in pharmaceutical preparations.

In WO 02/02508, a multistep manufacturing process to obtain δ-amino-γ-hydroxy-ω-aryl-alkanecarboxamides is described, in which the central intermediate is a 2,7-dialkyl-8-aryl-4-octenic acid or a 2,7-dialkyl-8-aryl-4-octenic acid ester. The double bond of this intermediate is simultaneously halogenated in the 4/5 position and hydroxylated in the 4-position via (under) halo-lactonisation conditions. The halolactone is converted to a hydroxy lactone and then the hydroxy group is converted to a leaving group, the leaving group is substituted with azide, the lactone amidated and then the azide is converted into the amine group.

Further processes for the preparation of intermediates to manufacture δ-amino-γ-hydroxy-ω-aryl-alkanecarboxamides are described in WO02/092828 pertaining to the preparation of 2-alkyl-5-halogenpent-4-ene carboxylic esters, WO 2001/009079 pertaining to the preparation of 2-alkyl-5-halogenpent-4-ene carboxylic acids, WO 02/08172 pertaining to the preparation of 2,7-dialkyl-4-hydroxy-5-amino-8-aryloctanoyl amides, WO 02/02500 pertaining to 2-alkyl-3-phenylpropionic acids, and WO02/024878 pertaining to 2-alkyl-3-phenylpropanols.

In EP-A-1215201 an alternative route to obtain δ-amino-γ-hydroxy-ω-aryl-alkanecarboxamides is disclosed. In GB-A-0511686.8 yet an alternative route route to obtain δ-amino-γ-hydroxy-ω-aryl-alkanecarboxamides is disclosed using a pyrrolidine intermediate.

Although the existing processes may lead to the desired renin inhibitors, in particular the 2(S),4(S),5(S),7(S)-2,7-dialkyl-4-hydroxy-5-amino-8-aryl-octanoyl amide derivatives, there exists a need to provide an alternative synthetic route to these 2(S),4(S),5(S),7(S)-2,7-dialkyl-4-hydroxy-5-amino-8-aryl-octanoyl amide derivatives to ensure its manufacture in a simple and efficient manner.

SUMMARY OF THE INVENTION

Surprisingly, it has now been found that renin inhibitors, in particular 2(S),4(S),5(S),7(S)-2,7-dialkyl-4-hydroxy-5-amino-8-aryl-octanoyl amide derivatives, are obtainable in high diastereomeric and enantiomeric purity and in an economic manner using a novel C-8 lactam lactone compound, in particular, a 5-(5-oxo-tetrahydro-furan-2-yl)pyrrolidin-2-one compound, as the starting material. In particular it was found that by using a C-8 lactam lactone compound, in particular, a 5-(5-oxo-tetrahydro-furan-2-yl)pyrrolidin-2-one compound as a chiral building block and introducing the organic aromatic moiety at the end of the synthesis, the process is more economic than the prior art processes where the organic aromatic moiety is introduced to the scaffold in early step of the synthesis sequences. Moreover, utilizing a C-8 lactam lactone compound conveniently locks and preserves the stereochemistry and, thus, simplifies the method of preparing such sophisticated types of molecules.

DETAILED DESCRIPTION OF THE INVENTION

Therefore in a first aspect, the present invention relates to a compound of the formula (II)

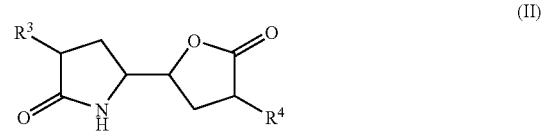

wherein $R^3$ is $C_{1-7}$alkyl or $C_{3-8}$cycloalkyl; and $R^4$ is $C_{1-7}$alkyl, $C_{2-7}$alkenyl, $C_{3-8}$cycloalkyl, phenyl- or naphthyl-$C_{1-4}$alkyl each unsubstituted or mono-, di- or tri-substituted by $C_{1-4}$alkyl, O—$C_{1-4}$alkyl, OH, $C_{1-4}$alkylamino, di-$C_{1-4}$alkylamino, halogen and/or by trifluoromethyl; or a salt thereof.

In a preferred embodiment, $R^3$ is $C_{1-7}$alkyl, preferably branched $C_{3-6}$alkyl, most preferably isopropyl.

In a preferred embodiment, $R^4$ is $C_{1-7}$alkyl, preferably branched $C_{3-6}$alkyl, most preferably isopropyl.

Preferably, the compound according to the formula (II) has the following stereochemistry:

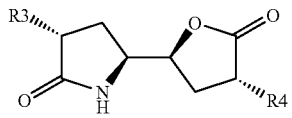

Most preferably, the compound of formula (II) has the following structure:

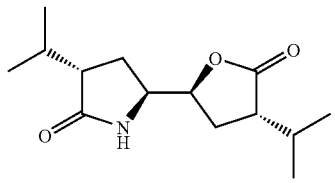

A compound of the formula (II) may be used, inter alia, for the synthesis of pharmaceutically active substances, preferably renin inhibitors such as aliskiren, especially as described in the following.

The present inventors have found convenient methods of preparing the key intermediate of the formula (II) as will be described in detail below. Any of the reaction steps either alone or in a suitable combination may be employed to yield the compound of the formula (II). Moreover, any of the following reaction steps either alone or in a suitable combination may be employed in the synthesis of a renin inhibitor, such as aliskiren.

Thus, in one aspect, the present invention relates to a method for preparing a compound of formula (II) as described above, said process comprising subjecting a compound of formula (I)

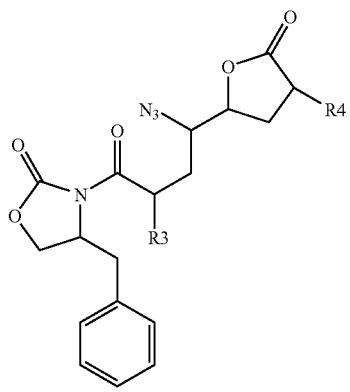

(I)

wherein $R^3$ and $R^4$ are as defined for a compound of formula (II), or a salt thereof, to hydrogenation to convert the azide moiety to an amine and to effect lactam ring closure. This process step as such, also forms an embodiment of the invention.

Preferred embodiments for $R^3$ and $R^4$ can be taken from the definitions for compounds of formula (II). Preferably, the compound according to the formula (I) has the following stereochemistry:

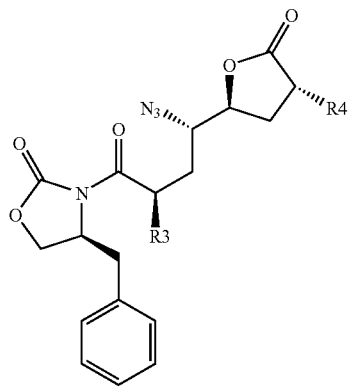

Compounds of the formula (I) can be obtained by methods well known in the art, in particular by following the procedures for preparing compound III in EP-A-0 678 514 which is incorporated herein by reference, in particular as disclosed in the working examples, especially example 2, in particular using conversion 2.c1.

Alternatively, a compound of formula (II) can be prepared using a different auxiliary than the one employed in the compound of formula (I).

Thus, in one aspect, the present invention relates to a method for preparing a compound of formula (II) as described above, said process comprising subjecting a compound of formula (I')

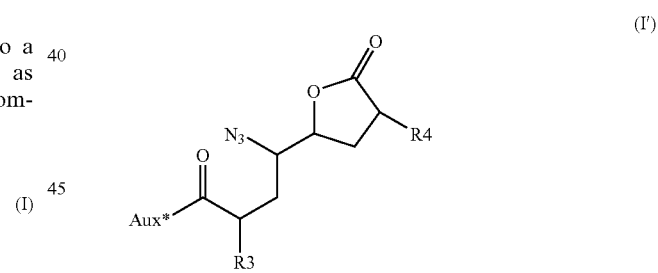

(I')

wherein $R^3$ and $R^4$ are as defined for a compound of formula (II) and Aux* is an auxiliary able to form an ester or amide with the carbonyl functionality, or a salt thereof, to hydrogenation to convert the azide moiety to an amine and to effect lactam ring closure. This process step as such, also forms an embodiment of the invention.

Preferred examples of Aux* include ephedrine compounds, oxazolidinone analogues, methylpyrrolidone analogues, carbohydrate analogues, and cyclic alcohols or amines. Typical examples include those described below as well as analogues thereof, in particular oxazolidone analogues, such as the Evans auxiliary or in more general terms chiral α-substituted oxazolidinone analogues. The literature for preparing these auxiliaries is mentioned below for further detail. Apart from the Evans auxiliary used in the compound of formula (I), ephedrine type auxiliaries and cyclic alcohol type auxiliaries such as (+)-fenchol, are preferred.

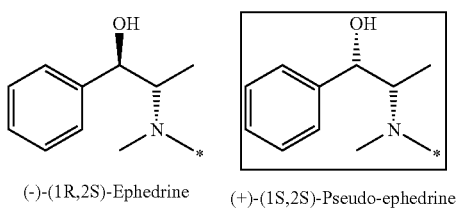

(-)-(1R,2S)-Ephedrine    (+)-(1S,2S)-Pseudo-ephedrine

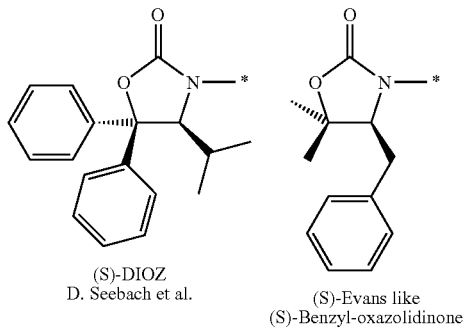

(S)-DIOZ
D. Seebach et al.

(S)-Evans like
(S)-Benzyl-oxazolidinone

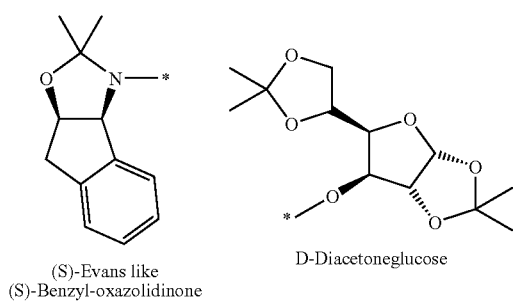

(S)-Evans like
(S)-Benzyl-oxazolidinone

D-Diacetoneglucose

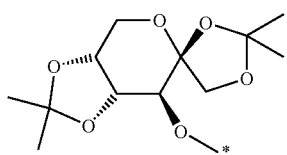

D-Diacetonefructose
L-DAF ex L-Sorbose

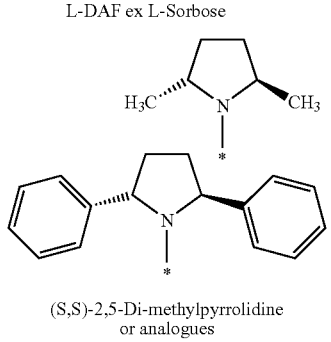

(S,S)-2,5-Di-methylpyrrolidine
or analogues

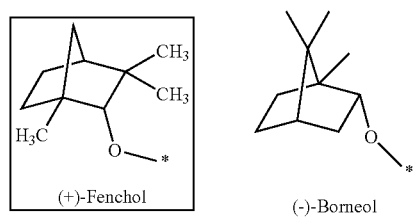

(+)-Fenchol    (-)-Borneol

-continued

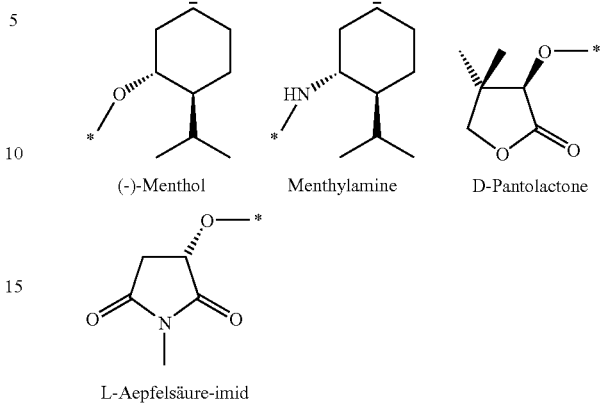

(-)-Menthol    Menthylamine    D-Pantolactone

L-Aepfelsäure-imid

Literature: 1.) K. Tadano et al., *Synlett*, 2004, (12), 2006
2.) Y. Shi et al., *Synthesis*, 2000, (14), 1979
3.) O. Piva et al., *Tetrahedron: Asymm.*: 16, 1513, (2005)
4.) H. J. Kim, et al., *Tetrahedron Lett.*, 46, 4115 (2005)

The compound of formula (I') can be prepared by following the experimental procedure as outlined in EP-A-0 678 514 for the Evans auxiliary. Thus, a suitable acid chloride represented by formula (I'i) such as 3-methyl-butyryl chloride (I'i)

wherein $R^3$ is as defined for a compound of formula (II), or a salt thereof, is reacted with the respective Aux*-H, wherein Aux* is as defined for a compound of formula (I') in the presence of a suitable base to obtain a compound of formula (I'ii)

(I'ii)

Similarly, the reaction can be conducted with an acid chloride of the formula (I'iii)

(I'iii)

wherein $R^4$ is as defined for a compound of formula (II), or a salt thereof, and the respective Aux*-H, wherein Aux* is as defined for a compound of formula (I') in the presence of a suitable base to obtain a compound of formula (I'iv)

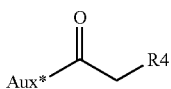 (I'iv)

The compounds of formula (I'ii) and (I'iv) are in turn reacted with (E)-1,4-Dibromo-but-2-ene of the formula (I'v)

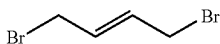 (I'v)

in the presence of a strong base to yield a compound of the formula (I'vi)

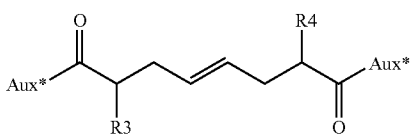 (I'vi)

wherein $R^3$ and $R^4$ are as defined for a compound of formula (II) and Aux* is as defined for a compound of formula (I'), or a salt thereof.

If $R^3$ and $R^4$ are identical, i.e. $R^3=R^4$, it is appreciated that 2 or more equivalents of a compound of formula (I'ii) are reacted with (E)-1,4-Dibromo-but-2-ene of the formula (I'v).

Thus a compound of the formula (I'vi)

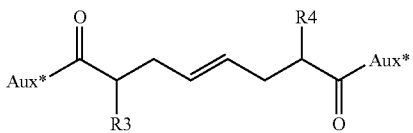 (I'vi)

wherein $R^3$ is $C_{1-7}$alkyl or $C_{3-8}$cycloalkyl;

$R^4$ is $C_{1-7}$alkyl, $C_{2-7}$alkenyl, $C_{3-8}$cycloalkyl, phenyl- or naphthyl-$C_{1-4}$alkyl each unsubstituted or mono-, di- or tri-substituted by $C_{1-4}$alkyl, O—$C_{1-4}$alkyl, OH, $C_{1-4}$alkylamino, di-$C_{1-4}$alkylamino, halogen and/or by trifluoromethyl; and Aux* is an auxiliary able to form an ester or amide with the carbonyl functionality; or a salt thereof, is a valuable intermediate of the process of preparing renin inhibitors such as aliskiren, in an efficient manner. Therefore such compounds as well as the method of obtaining compound (II) using this intermediate (I'vi) also form an embodiment of the invention.

The compound of formula (I'vi) is further reacted with a halogenation agent such as NCS, NBS, NIS (all N-halosuccinimides), $Br_2$ or bromohydantoin, using halolactonization reaction conditions to form a compound of formula (I'vii)

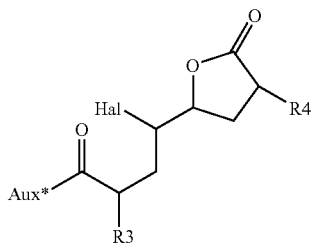 (I'vii)

wherein $R^3$ and $R^4$ are as defined for a compound of formula (II), Aux* is as defined for a compound of formula (I') and Hal is a halogen, or a salt thereof.

The halogen functionality of the compound of formula (I'vii) is then converted into an azide by inversion using a $N_3^-$ source to obtain the compound of formula (I'). Examples of the $N_3^-$ source include standard reagents such as $LiN_3$, $NaN_3$, $KN_3$, $MeN_3$, alkyl ammonium azides of the type $(alkyl)_4NN_3$ or $(alkyl)_3NHN_3$ or e.g. tetraalkylguanidinium azides or organometalic azides. The reaction proceeds under conditions well known in the art such as in a homogeneous or biphasic solvent mixture or in ionic liquids or mixtures of an ionic liquid. Preferably, the reaction takes place at temperatures in the range of 0 to 120° C., such as 20 to 100° C., preferable 50 to 80° C.

The reaction to convert the azide moiety of the compound of formula (I) or (I') to an amine and to effect lactam ring closure preferably takes place under conditions so as to keep the other functionalities on the molecule intact. Hydrogenation typically takes place in the presence of a catalyst selected from a heterogeneous catalyst or a homogeneous catalyst, such as Wilkinson's catalyst, preferably a heterogeneous catalyst. Examples of the catalyst include Raney nickel, palladium/C, $Pd(OH)_2$ (Perlman's catalyst), nickel boride, platinum metal or platinum metal oxide, rhodium, ruthenium and zinc oxide, more preferably palladium/C, platinum metal or platinum metal oxide, most preferably palladium/C. The catalyst is preferably used in an amount of 1 to 20%, more preferably 5 to 10%. The reaction can be conducted at atmospheric or elevated pressure, such as a pressure of 2-10 bar, e.g. 5 bar, more preferably the reaction is conducted at atmospheric pressure. The hydrogenation takes place preferably in an inert solvent, more preferably in tetrahydrofuran or toluene. Also suitable are protic solvents, such as alcohol, e.g. ethanol or methanol, or ethyl acetate. These solvents may be used in the presence of water. The reaction time and the temperature are chosen so as to bring the reaction to completion at a minimum time without the production of unwanted side products. Typically the reaction can be conducted at 0° C. to reflux, preferably 0 to 60° C., such as 0 to 40° C., more preferably 15-30° C., such as room temperature, for 10 min to 12 h, preferably 20 min to 6 h, most preferably 30 min to 4 h, such as 1 to 3 h or 6 to 12 h.

During the hydrogenation of compound (I) or (I') stoichiometric amounts of the protonated auxiliary Aux*-H, such as the oxazolidinone, namely the chiral auxiliary (e.g. (S)-Evans reagent) are split off. Because both compounds (II) and the auxiliary, such as the Evans auxiliary, are both crystalline and have similar properties, it is preferred to separate both compounds and at the same time recycle the expensive auxiliary by a simple separation technique (crystallization or extraction). It was found that by saponification of the lactone ring of the lactam lactone (II) a transfer into the aqueous phase is possible due to lactone ring opening whereas the oxazolidinone (or the auxiliary in general) stays in the organic phase. By simple phase separation followed by acidification of the water phase a re-lactonisation is possible, which allows the isolation of pure compound (II). Saponification is preferably achieved by treatment with bases like organic or inorganic bases, preferably inorganic bases. Examples include LiOH or NaOH. The saponification is typically conducted in a suitable solvent. Examples include aqueous systems or aqueous/organic solvent mixtures and even organic solvents such as alcohols or toluene, whereby alcohol/water mixtures, such as ethanolic/aqueous solutions, are preferred. After phase separation, the aqueous phase is typically acidified to protonate the γ-hydroxy acid salt and to obtain the γ-hydroxy acid in the free form. Typical acids suitable for the acidification are chosen so that they are stronger than the γ-hydroxy acid but keep the other functionalities on the molecule intact. Suitable acids include organic acids, such as citric acid, tartaric acid or similar acids, or dilute inorganic acids such as dilute HCl. The free acid will re-form the lactone (II), preferably by heating the mixture to e.g. 30 to 80° C., more preferably 40 to 60° C., such as 50° C.

Thus a compound of the formula (II')

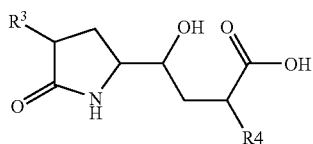

(II')

wherein $R^3$ is $C_{1-7}$alkyl or $C_{3-8}$cycloalkyl; and $R^4$ is $C_{1-7}$alkyl, $C_{2-7}$alkenyl, $C_{3-8}$cycloalkyl, phenyl- or naphthyl-$C_{1-4}$alkyl each unsubstituted or mono-, di- or tri-substituted by $C_{1-4}$alkyl, O—$C_{1-4}$alkyl, OH, $C_{1-4}$alkylamino, di-$C_{1-4}$alkylamino, halogen and/or by trifluoromethyl; or a salt thereof, is a valuable intermediate of the process of preparing renin inhibitors such as aliskiren, in an efficient manner. Therefore such compounds as well as the method of obtaining compound (II) using this intermediate (II') also form an embodiment of the invention.

Preferred embodiments of compound (II) are also preferred for compound (II'). In particular the following stereochemistry is preferred:

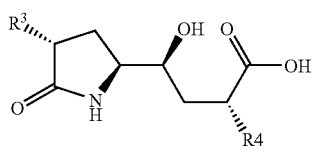

Preferably, the compound has the following formula

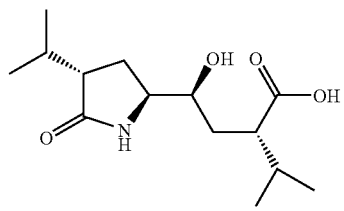

As an alternative approach to obtain the compound of the formula (II), the present invention relates in another aspect to a method for preparing a compound of formula (II) as defined above, said process comprising subjecting a compound of formula (III)

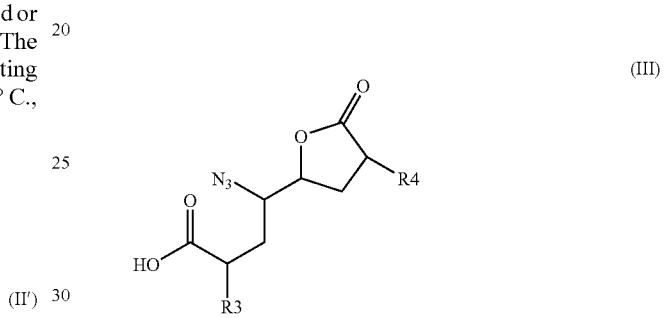

(III)

wherein $R^3$ and $R^4$ are as defined for a compound of formula (II), or a salt thereof, to conversion to an anhydride of formula (IV)

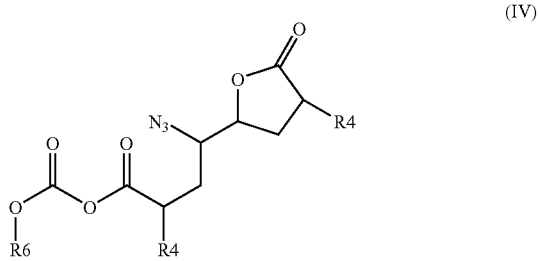

(IV)

wherein $R^3$ and $R^4$ are as defined for a compound of formula (II) and $R^6$ is $C_{1-7}$alkyl or $C_{3-8}$cycloalkyl, or a salt thereof; to activate the acid moiety followed by hydrogenation to convert the azide moiety to an amine and to effect lactam ring closure. This process step as such as well as the compound of formula (IV), also forms an embodiment of the invention.

Preferred embodiments for $R^3$ and $R^4$ can be taken from the definitions for compounds of formula (II).

In a preferred embodiment, $R^6$ is $C_{1-7}$alkyl, more preferably straight chain or branched $C_{1-4}$ alkyl, most preferably methyl, ethyl, isopropyl or isobutyl.

Preferably, the compound according to the formula (IV) has the following stereochemistry:

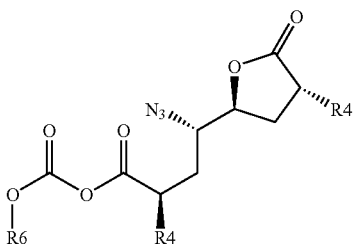

Compounds of the formula (III) can be obtained by methods well known in the art, in particular from compounds of the formula (I) as defined above by following the procedures for preparing such compounds in EP-A-0 678 514 which is incorporated herein by reference, in particular as disclosed in the working examples, especially example 3. Analogously, compounds of formula (I') can be converted to compounds of formula (II) following these procedures.

Both conversions may be conducted as separate steps by isolating the anhydride of the formula (IV) or by conducting them as a one-pot synthesis without isolation. Preferably the reaction mixture obtained after the formation of the anhydride of the formula (IV) is directly subjected to hydrogenation.

The reaction of the compound of the formula (III) to form the mixed anhydride of formula (IV) to activate the acid moiety preferably takes place under conditions so as to keep the other functionalities on the molecule intact. The anhydride is typically introduced using an activated acid, such as an acid chloride $R^6$—CO—Cl. It is preferred to add the activated acid over a certain period of time. Preferably the reaction is conducted under basic or acidic conditions, more preferably basic conditions. Suitable bases include organic or inorganic bases, preferably organic bases, more preferably a nitrogen base, yet more preferably a tertiary nitrogen base. Examples of the tertiary nitrogen base include trimethylamine, DBU, triethylamine and diisopropylethylamine. The reaction can be conducted in any suitable solvent, preferably an aprotic solvent such as ether, in particular THF and TBME, an aromatic or a halogenated solvent, more preferably THF or toluene. The reaction time and the temperature are chosen so as to bring the reaction to completion at a minimum time without the production of unwanted side products. Typically the reaction can be conducted at −20° C. to reflux, preferably −10 to 40° C., more preferably 0-30° C., such 0 to 10° C., for 1 min to 12 h, preferably 10 min h to 4 h, most preferably 15 min to 2 h, such as 30 min to 1 h.

Reference is made to standard procedures well known to the person in the art and as described e.g. in Houben-Weyl, Vol. E5/2 (1985), p. 934-1183, Houben-Weyl, Vol. E5/1 (1985), p. 193-773, and Houben-Weyl, Vol. 8 (1952), p. 359-680, which are incorporated herein by reference.

The reaction of the compound of the formula (IV) to convert the azide moiety to an amine and to effect lactam ring closure preferably takes place under conditions so as to keep the other functionalities on the molecule intact. Hydrogenation typically takes place in the presence of a catalyst selected from a heterogeneous catalyst or a homogeneous catalyst, such as Wilkinson's catalyst, preferably a heterogeneous catalyst. Examples of the catalyst include Raney nickel, palladium/C, Pd(OH)$_2$ (Perlman's catalyst), nickel boride, platinum metal or platinum metal oxide, rhodium, ruthenium and zinc oxide, more preferably palladium/C, platinum metal or platinum metal oxide, most preferably palladium/C. The catalyst is preferably used in an amount of 1 to 20%, more preferably 5 to 10%. The reaction can be conducted at atmospheric or elevated pressure, such as a pressure of 2-10 bar, e.g. 5 bar, more preferably the reaction is conducted at atmospheric pressure. The hydrogenation takes place preferably in an inert solvent, more preferably in tetrahydrofuran or toluene. The reaction time and the temperature are chosen so as to bring the reaction to completion at a minimum time without the production of unwanted side products. Typically the reaction can be conducted at 0° C. to reflux, preferably 0 to 40° C., more preferably 15-30° C., such as room temperature, for 30 min to 48 h, preferably 2 h to 36 h, most preferably 12 min to 24 h, such as 17 to 23 h.

As yet an alternative approach to obtain the compound of the formula (II), the present invention relates in another aspect to a method for preparing a compound of formula (II) as defined above, said process comprising subjecting a compound of formula (III)

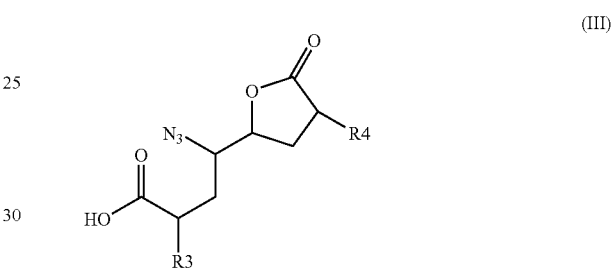

wherein $R^3$ and $R^4$ are as defined for a compound of formula (II), or a salt thereof, to conversion to an ester of formula (V)

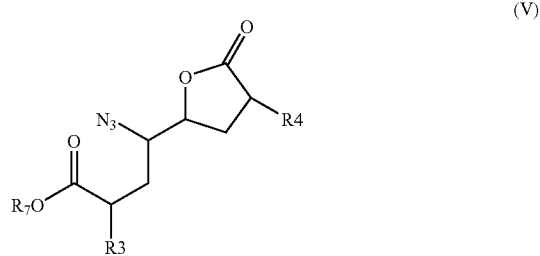

wherein $R^3$ and $R^4$ are as defined for a compound of formula (II) and $R^7$ is $C_{1-7}$alkyl or $C_{3-8}$cycloalkyl, or a salt thereof; followed by hydrogenation to convert the azide moiety to an amine and to effect lactam ring closure. This process step as such as well as the compound of formula (V) also forms an embodiment of the invention.

Preferred embodiments for $R^3$ and $R^4$ can be taken from the definitions for compounds of formula (II).

In a preferred embodiment, $R^7$ is $C_{1-7}$alkyl, more preferably straight chain or branched $C_{1-4}$alkyl, most preferably methyl, ethyl, n-propyl, isopropyl, n-butyl, t-butyl or isobutyl.

Preferably, the compound according to the formula (V) has the following stereochemistry:

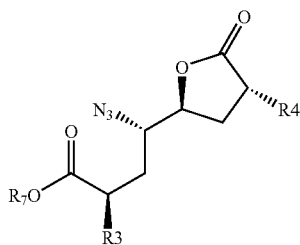

Compounds of the formula (III) which are used as starting materials for this conversion can be obtained as described above.

Both conversions may be conducted as separate steps by isolating the ester of the formula (V) or by conducting them as a one-pot synthesis without isolation. Preferably the reaction mixture obtained after the formation of the ester of the formula (V) is directly subjected to hydrogenation.

The reaction of the compound of the formula (III) to form the ester of formula (V) preferably takes place under conditions so as to keep the other functionalities on the molecule intact. The ester is typically introduced by converting the acid (III) to an activated acid, such as an acid chloride with a suitable reagent such a $SOCl_2$. Alternatively, the ester can be introduced in a fast and efficient manner by employing a suitable $R^7$-triazene as the alkyl donor with the concomitant evolution of nitrogen. Examples of the triazene include aryl triazenes such as 3-methyl-1-(p-tolyl)-triazene. The reaction can be conducted preferably under neutral conditions. The reaction can be conducted in any suitable solvent, preferably an aprotic solvent such as ether, such as THF or TBME, an aromatic or a halogenated solvent, more preferably THF, methylene chloride or toluene. The reaction time and the temperature are chosen so as to bring the reaction to completion at a minimum time without the production of unwanted side products. Typically the reaction can be conducted at 0° C. to reflux, preferably 10 to 40° C., more preferably 15-30° C., such as room temperature, for 1 min to 12 h, preferably 10 min h to 6 h, most preferably 30 min to 4 h, such as 2 to 3 h or until all nitrogen evolution has stopped. Several other procedures for making esters from carboxylic acid are described for example in: Organicum, Wiley-VCH, Ed. 20, (1999) p. 442 which is incorporated herein by reference.

The reaction of the compound of the formula (V) to convert the azide moiety to an amine and to effect lactam ring closure preferably takes place under conditions so as to keep the other functionalities on the molecule intact. Hydrogenation typically takes place in the presence of a catalyst selected from a heterogeneous catalyst or a homogeneous catalyst, such as Wilkinson's catalyst, preferably a heterogeneous catalyst. Examples of the catalyst include Raney nickel, palladium/C, $Pd(OH)_2$ (Perlman's catalyst), nickel boride, platinum metal or platinum metal oxide, rhodium, ruthenium and zinc oxide, more preferably palladium/C, platinum metal or platinum metal oxide, most preferably palladium/C. The catalyst is preferably used in an amount of 1 to 20%, more preferably 5 to 10%. The reaction can be conducted at atmospheric or elevated pressure, such as a pressure of 2-10 bar, e.g. 5 bar, more preferably the reaction is conducted at atmospheric pressure. The hydrogenation takes place preferably in an inert solvent, more preferably in tetrahydrofuran or toluene. The reaction time and the temperature are chosen so as to bring the reaction to completion at a minimum time without the production of unwanted side products. Typically the reaction can be conducted at 0° C. to reflux, preferably 0 to 40° C., more preferably 15-30° C., such as room temperature, for 30 min to 48 h, preferably 2 h to 36 h, most preferably 12 to 24 h, such as 17 to 23 h.

The different approaches to obtain the compound of formula (II) are summarized below in Scheme 1:

Scheme 1: Routes to C-8 lactam lactone of formula (II)

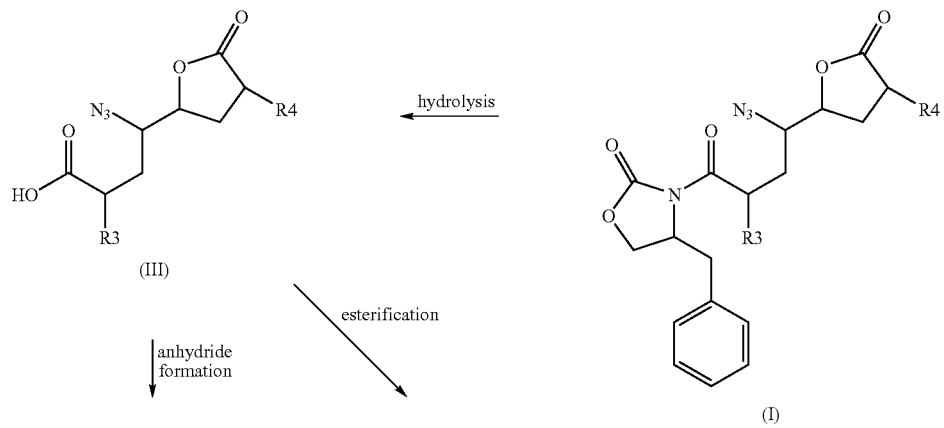

-continued

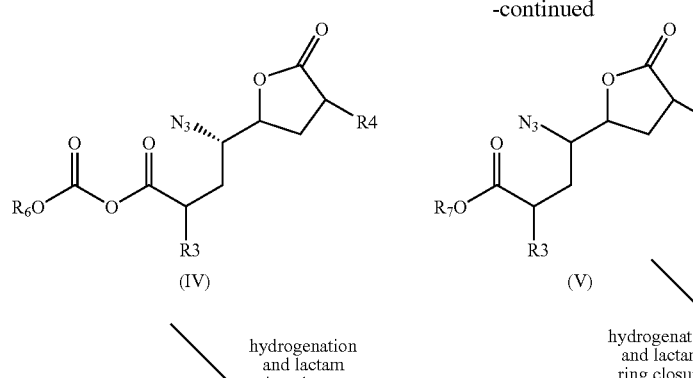

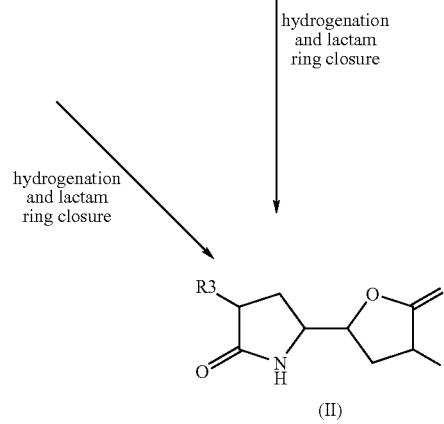

Scheme 1 exemplifies as the auxiliary the Evans auxiliary but other auxiliaries as outlined for compound (I') are also possible. Thus, the same routes to the C-8 lactam lactone of formula (II) as shown in Scheme 1 apply by using the compound of formula (I') as the starting material.

In a preferred further embodiment of the invention, this synthesis comprises as a further step or as an individual synthesis the preparation of a compound of formula (VI)

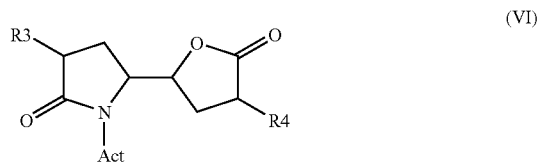

wherein $R^3$ and $R^4$ are as defined for a compound of formula (II) and Act is an activating group selected from an amino protecting group, in particular a carbamate, or a salt thereof; comprising introducing the activating group at the nitrogen of a compound of formula (II), or a salt thereof. This process step as such as well as compounds of formula (VI) also form embodiments of the invention.

This conversion proceeds under standard conditions and as described e.g. in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974 which are incorporated herein by reference.

In particular when Act is an alkoxy carbonyl group so as to form a carbamate, the reaction is preferably conducted under basic conditions. The base can be used stoichiometrically or catalytically. Suitable bases include organic or inorganic bases, preferably organic bases, more preferably a nitrogen base, yet more preferably a tertiary nitrogen base. Examples of the tertiary nitrogen base include triethylamine, diisopropylethylamine, DBU, TMEDA and trimethylamine. DMAP can be used as a catalyst. The reaction can be conducted in any suitable solvent, preferably a polar solvent such as an ethyl acetate or isopropyl acetate, an ether, such as THF or TBME, or a halogenated solvent, more preferably THF, methylene chloride or isopropyl acetate. The reaction time and the temperature are chosen so as to bring the reaction to completion at a minimum time without the production of unwanted side products. Typically the reaction can be conducted at 0° C. to reflux, preferably 0 to 60° C., more preferably 15-50° C., such as 20-45° C., for 10 min to 36 h, preferably 3 h to 24 h, most preferably 6 h to 24 h, such as 12-17 h.

Another important embodiment of the invention relates to a compound of the formula (VI)

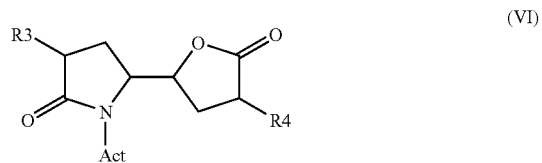

wherein $R^3$ is $C_{1-7}$alkyl or $C_{3-8}$cycloalkyl;

$R^4$ is $C_{1-7}$alkyl, $C_{2-7}$alkenyl, $C_{3-8}$cycloalkyl, phenyl- or naphthyl-$C_{1-4}$alkyl each unsubstituted or mono-, di- or tri-substituted by $C_{1-4}$alkyl, O—$C_{1-4}$alkyl, OH, $C_{1-4}$alkylamino, di-$C_{1-4}$alkylamino, halogen and/or by trifluoromethyl; and Act is an activating group selected from an amino protecting group, in particular a carbamate; or a salt thereof. In another preferred embodiment, Act is an acyl or a substituted sulfonyl group.

In a preferred embodiment, $R^3$ is $C_{1-7}$alkyl, preferably branched $C_{3-6}$alkyl, most preferably isopropyl.

In a preferred embodiment, $R^4$ is $C_{1-7}$alkyl, preferably branched $C_{3-6}$alkyl, most preferably isopropyl.

In a preferred embodiment, Act is an N-protecting group, for example, an amino protecting group which is conventionally used in peptide chemistry (cf.: "Protective groups in Organic Synthesis", 5$^{th}$. Ed. T. W. Greene & P. G. M. Wuts, which is incorporated herein by reference), especially in the chemistry of protecting pyrrolidines. In the following the terminology "Act" is maintained throughout the synthesis sequence for sake of consistency. It is appreciated that "Act" serves as an activating group when present on the lactam nitrogen and that after lactam opening the Act group is a protecting group.

Preferred protecting groups comprise, for example, (i) $C_1$-$C_2$-alkyl that is mono-, di- or trisubstituted by phenyl, such as benzyl, (or) benzhydryl or trityl, wherein the phenyl ring is unsubstituted or substituted by one or more, e.g. two or three, residues e.g. those selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; phenyl-$C_1$-$C_2$-alkoxycarbonyl; and allyl or cinnamyl. Especially preferred are benzyloxycarbonyl (Cbz), 9-fluorenylmethyloxycarbony (Fmoc), benzyloxymethyl (BOM), pivaloyl-oxy-methyl (POM), trichloroethoxycarbonyl (Troc), 1-adamantyloxycarbonxyl (Adoc), but can also be benzyl, cumyl, benzhydryl, trityl, allyl, $C_{1-10}$ alkenyloxy carbonyl, such as alloc (allyloxycarbonyl). The protecting group can also be silyl, like trialklysilyl, especially trimethylsilyl, tert.-butyl-dimethylsilyl, triethylsilyl, triisopropylsilyl, trimethylsilyethoxymethyl (SEM), and can also be substituted sulfonyl (e.g. $C_1$-$C_7$alkyl, aryl such as phenyl, substituted aryl such as with $C_1$-$C_7$-alkyl, halo, hydroxyl or $C_1$-$C_7$-alkoxy substituted phenyl, in particular tosyl (4-methyl-phenyl sulfonyl), or camphorsulfonyl) or substituted sulfenyl (subst.arylsulfenyl). For the use of sulfonyl and acyl groups it is referred to D. Savoia, et al., J. Org. Chem., 54, 228 (1989), and literature cited there.

Examples for Act include $C_{1-10}$ alkenyloxy carbonyl, $C_{6-10}$aryl-$C_{1-6}$alkyl, and $C_{1-6}$alkyl-carbonyl, $C_{6-10}$aryl-carbonyl, $C_{1-6}$alkoxy-carbonyl, $C_{6-10}$aryl-$C_{1-6}$alkoxycarbonyl, $C_{1-6}$alkyl-sulfonyl, or $C_{6-10}$aryl-sulfonyl, such as $C_{1-10}$ alkenyloxy carbonyl, $C_{6-10}$aryl-$C_{1-6}$alkyl, and $C_{1-6}$alkyl-carbonyl, $C_{6-10}$aryl-carbonyl, $C_{1-6}$alkoxy-carbonyl, and $C_{6-10}$aryl-$C_{1-6}$alkoxycarbonyl. In a preferred embodiment, Act is $C_{6-10}$aryl-$C_{1-6}$alkoxycarbonyl, $C_{1-6}$alkoxy-carbonyl, allyloxycarbonyl or $C_{6-10}$aryl-$C_{1-6}$alkyl such as benzyl, t-butoxycarbonyl or benzyloxycarbonyl. In a preferred embodiment, Act is t-butoxy- or benzyloxycarbonyl.

Preferably, the compound according to the formula (VI) has the following stereochemistry:

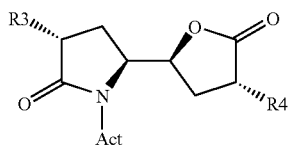

More preferably, the compound of formula (VI) has the following structure:

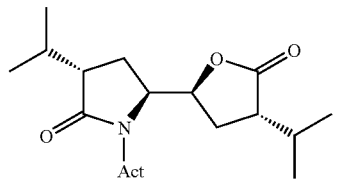

Most preferably, the compound of formula (VI) has the following structure:

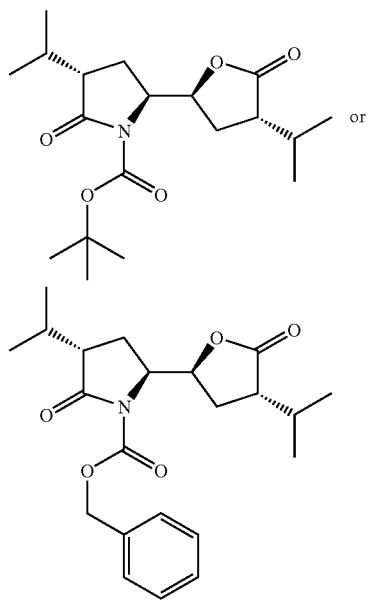

or

A compound of the formula (VI) may be used, inter alia, for the synthesis of pharmaceutically active substances, preferably renin inhibitors such as aliskiren, especially as described in the following.

In a preferred further embodiment of the invention, this synthesis comprises as a further step or as an individual synthesis the preparation a compound of formula (VIII)

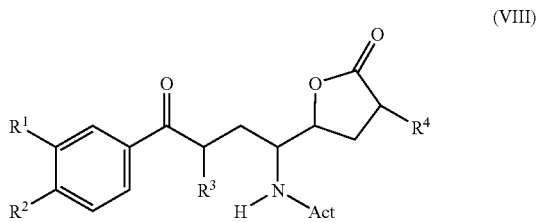

(VIII)

wherein $R^3$ and $R^4$ are as defined for a compound of formula (II) and Act is an activating group selected from an amino protecting group, in particular a carbamate, $R^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl; $R^2$ is halogen, hydroxyl, $C_{1-4}$alkyl or $C_{1-4}$alkoxy, or a salt thereof;

comprising the step of lactam ring opening of the N-activated lactam lactone of formula (VI) or a salt thereof defined above with a compound of formula (VII)

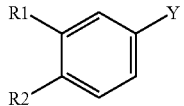
(VII)

wherein Y is a metal containing group such as —Li, —MgX, -magnesates, aryl magnesium species such as

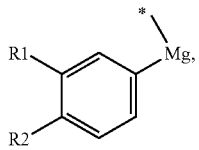

wherein R1 and R2 are as defined herein, alkyl magnesium species, such as branched $C_{1-7}$alkyl-Mg—, —MnX, (alkyl)$_3$MnLi—, or —CeX$_2$, wherein X is halogen such as Cl, I or Br, more preferably Br; and $R^1$ and $R^2$ are as defined for a compound of formula (VIII) above. This process step as such as well as the compounds (VIII) and (VII) also form embodiments of the invention. For this conversion, see also D. Savoia, et al., J. Org. Chem., 54, 228 (1989), and literature cited there.

Preferred embodiments for $R^3$, $R^4$ and Act for compound of formula (VIII) can be taken from the definitions for compounds of formula (VI).

In a preferred embodiment, $R^1$ is hydroxyl, $C_{1-6}$alkoxy-$C_{1-6}$ alkyloxy or $C_{1-6}$alkoxy-$C_{1-6}$alkyl, more preferably $C_{1-4}$alkoxy-$C_{1-4}$alkyloxy, most preferably methoxypropoxy.

In a preferred embodiment, $R^2$ is hydroxyl or $C_{1-4}$alkoxy, more preferably branched $C_{1-4}$alkoxy, most preferably methoxy.

Preferably, the compound according to the formula (VIII) has the following stereochemistry:

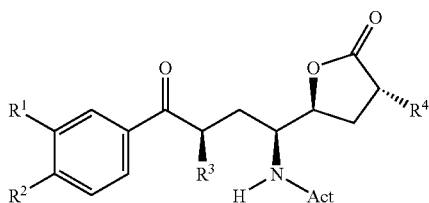

Preferred examples the compound according to the formula (VIII) have the following formula:

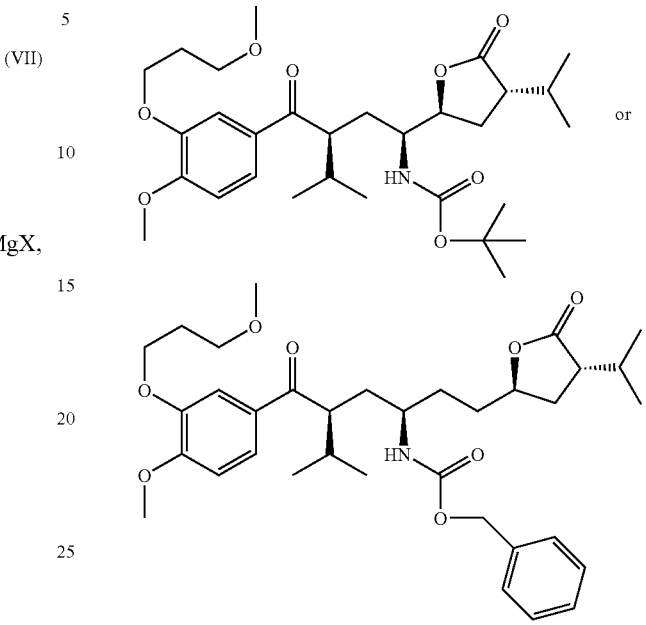

Compounds of formula (VII) are obtainable from compounds of formula (VII'), preferably in situ:

(VII')

wherein X is halogen such as Cl, I or Br, more preferably Br; and $R^1$ and $R^2$ are as defined for a compound of formula (VIII) above.

Compounds of formula (VII) can be prepared according to methods well known to the person skilled in the art, in particular halogen metal exchange procedures, e.g. as described in the following literature references describing several different approaches:

Lit. 1: for magnesates: a) K. Oshima et al., Angew. Chem., Int. Ed. 2000, 39, 2481 and lit. cited therein. b) K. Oshima et al.; J. Organomet. Chem., 1999, 575, 1-20. c) K. Oshima et al., J. Org. Chem., 66, 4333 (2001); d) A. Akao et al., Tetrahedron Lett., 47, 1877 (2006);

e) K. Ishihara et al., Org. Lett., 7, 573 (2005), reports addition of trialkyl MgLi-magnesates to carbonyl groups; f) T. Mase et al., Tetrahedron Lett., 42, 4841 (2001).

Lit. 2: for Grignard reagents:
a) P. Knochel et al., Angew. Chem. Int. Ed 2000, 39, 4414
b) P. Knochel et al., Angew. Chem. Int. Ed. 2003, 42, 4438
c) Houben-Weyl, Vol. 13/2a, page 53-526
d) P. Knochel et al.; Synthesis 2002, 565,
e) P. Knochel et al., Angew. Chem., 118, 165 (2006), electron rich diaryl Mg compounds
f) S. Hall et al., Heterocycles, 24, 1205 (1987), direct Li-halogen exchange with Li metal g) Pat. Appl.; DE 10240262 A1, 2004 Mar. 11, direct Li-halogen exchange with Li metal
h) C. Feugeas, Bull. Soc. Chim. Fr., (8) 1892-1895 (1964); direct action of Mg metal to electron rich bromo aryl compounds to give electron rich Mg compounds
i) C. Feugeas, Comptes Rendus, 90, (1), 113-116 (1965); direct action of Mg metal to electron rich bromo aryl compounds
j) B. Bogdanovic et al., Angew. Chem., Int. Ed., 39, 4610 (2000)
k) *Handbook of Grignard Reagents* (Eds. G. S. Silverman, P. E. Rakita) Marcel Dekker, New York, 1996
l) N. Krause, "*Metallorganische Chemie*", Spektrum Akademischer Verlag, Heidelberg, 1996, Chapter 3
m) "Grignard Reagents—New Developments", Ed. H. G. Richey, John Wiley & Sons, Chichester, 2000.

all of which are incorporated herein by reference.

Typically, the organometallic species (VII) is prepared from compound (VII') according to the different literature mentioned above. Usually the reaction takes place in an inert solvent, more preferably in tetrahydrofuran, other ethers or toluene, or in solvent mixtures such as mixtures of ethers like THF and alkanes like hexane, heptane or cyclohexane. The reaction time and the temperature are chosen so as to bring the reaction to completion at a minimum time without the production of unwanted side products. Typically the reaction can be conducted at low temperatures or at room temperature, such as 0 to 30° C., more preferably 0 to 20° C. In one embodiment, the reaction can be conducted at 0° C. or below, preferably −80 to −20° C., more preferably −80 to −40° C., such as −78 to −50° C., for 30 min h to 10 h, preferably 1 h to 5 h, most preferably 1.5 to 4 h, such as 2 to 3 h.

The special challenge in the case of compound (VIII) reacting with a metallo organic species like (VII') lies in the chemo selective differentiation between reaction at the lactam moiety versus the lactone moiety. By introducing an activating group Act at the lactam nitrogen, it was found by the present inventors that surprisingly only the lactam ring is opened and the lactone stays intact.

Compounds of formula (VII) were found to be important reagents in the above conversion and, thus, the synthesis of renin inhibitors. Therefore, in one aspect the present invention also relates to a compound of formula (VII)

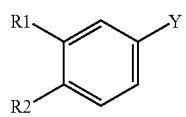

(VII)

wherein Y is a metal containing group such as —Li, —MgX, -magnesates, aryl magnesium species such as

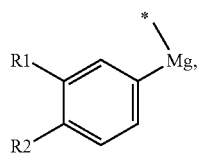

wherein R1 and R2 are as defined herein, alkyl magnesium species, such as branched $C_{1-7}$alkyl-Mg—, —MnX, (alkyl)$_3$MnLi—, or —CeX$_2$ wherein X is halogen such as Cl, I or Br, more preferably Br; R$^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl; and R$^2$ is halogen, hydroxyl, $C_{1-4}$alkyl or $C_{1-4}$alkoxy; or a salt thereof. Such compounds make it possible to connect the aromatic moiety of the renin inhibitor to the carbon chain in an efficient manner.

Preferably Y is Li, a magnesate or MgBr, more preferably Li or MgBr, still more preferably MgBr. Preferably the compounds of formula (VII) have the following structures:

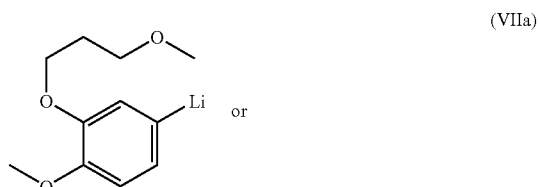

(VIIa)

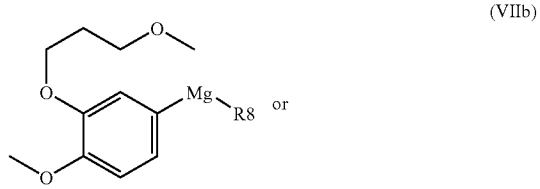

(VIIb)

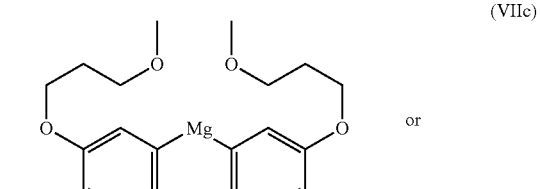

(VIIc)

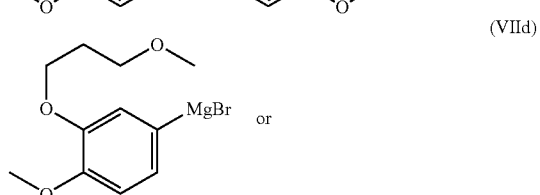

(VIId)

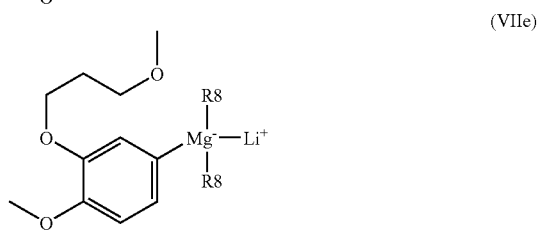

(VIIe)

R8 = $C_{1-7}$ alkyl, preferably branched C1-7 alkyl

In one embodiment, compounds having the following structure are preferred:

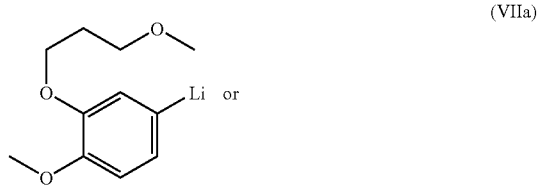

(VIIa)

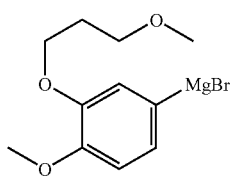
(VIId)

Preferably the compound of formula (VII') has the following structure:

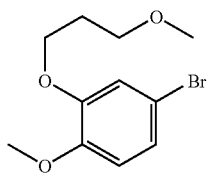

After the conversion of compound (VI) to compound (VIII) it is preferred to separate compound (VIII) in a simple and convenient manner without extensive purification techniques. Similar as in the work-up of compound (II) it was found that by saponification of the lactone ring of the compound (VIII) a transfer into the aqueous phase is possible due to lactone ring opening whereas possible by-products stay in the organic phase. By simple phase separation followed by acidification of the water phase a re-lactonisation is possible, which allows the isolation of pure compound (VIII). Saponification is preferably achieved by treatment with bases like organic or inorganic bases, preferably inorganic bases. Examples include LiOH, NaOH, $K_2CO_3$ or $Na_2CO_3$, preferably LiOH or NaOH. The saponification is typically conducted in a suitable solvent. Examples include aqueous systems or aqueous/organic solvent mixtures and even organic solvents such as alcohols or toluene, whereby alcohol/water mixtures, such as ethanolic/aqueous solutions, are preferred. After phase separation, the aqueous phase is typically acidified to protonate the γ-hydroxy acid salt to obtain the γ-hydroxy acid in the free form. Typical acids suitable for the acidification are chosen so that they are stronger than the γ-hydroxy acid but keep the other functionalities on the molecule, in particular the Act group, intact. Suitable acids include organic acids, such as citric acid, tartaric acid, oxalic acid or similar acids, or dilute inorganic acids such as dilute HCl. The free acid will re-form the lactone moiety of compound (VIII), preferably by heating the mixture to e.g. 30 to 80° C., more preferably 40 to 60° C., such as 50° C.

Thus a compound of the formula (VIII')

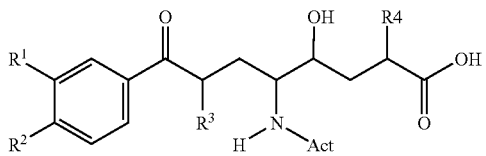
(VIII')

wherein $R^3$ is $C_{1-7}$alkyl or $C_{3-8}$cycloalkyl;

$R^4$ is $C_{1-7}$alkyl, $C_{2-7}$alkenyl, $C_{3-8}$cycloalkyl, phenyl- or naphthyl-$C_{1-4}$alkyl each unsubstituted or mono-, di- or tri-substituted by $C_{1-4}$alkyl, O—$C_{1-14}$alkyl, OH, $C_{1-4}$alkylamino, di-$C_{1-14}$alkylamino, halogen and/or by trifluoromethyl;

$R^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl;

$R^2$ is halogen, hydroxyl, $C_{1-4}$alkyl or $C_{1-4}$alkoxy; and

Act is an activating group selected from an amino protecting group, in particular a carbamate; or a salt thereof; is a valuable intermediate of the process of preparing renin inhibitors such as aliskiren, in an efficient manner. Therefore such compounds as well as the method of obtaining compound (VIII) using this intermediate (VIII') also form an embodiment of the invention.

Particularly preferred examples of the compound of formula (VIII') include a salt, namely a carboxylate salt. Preferred examples include inorganic salts such as alkaline and alkaline earth metal salts, such as Li, Na, K, Mg, Ca salts, or organic salts, such as primary, secondary or tertiary amine salts. Examples of primary amines include $C_{3-8}$cycloalkylamines such as cyclohexylamine, primary aromatic amines, such as aniline, aryl alkyl amines such as benzylamine and including aryl branched alkyl amines such as phenyl- or naphthylethylamine. Secondary amines include N di-substituted ($C_{1-7}$alkyl, $C_{3-8}$cycloalkyl, phenyl, and/or phenyl-$C_{1-4}$alkyl) amines such as di($C_{1-7}$alkyl) amines or dicyclohexylamine. Tertiary amines include N tri-substituted ($C_{1-7}$alkyl, $C_{3-8}$cycloalkyl, phenyl, and/or phenyl-$C_{1-4}$alkyl) amines. Particularly preferred is the Li salt.

The advantage of using the compound of formula (VIII') in the form of the salt is the opportunity to yield a solid, preferably a crystalline, material that is easier to handle in the production process. Another advantage is that a broader range of reducing agents can be employed for the reduction of the C8 carbonyl group when the C1 carbonyl is a salt of a carboxylic acid and not part of a lactone.

Such a salt can be obtained by standard procedures known in the art and as described in the examples. As one method, the salt is obtained directly from the saponification after ring opening of the compound of formula (VIII) with the respective base as described above. Alternatively, the free acid of formula (VIII') can be basified to deprotonate the γ-hydroxy acid salt to obtain the γ-hydroxy acid in the salt form. Typical bases suitable for the salt formation are chosen so that they convert the acid to the salt but keep the other functionalities on the molecule, in particular the Act group, intact. Suitable bases include inorganic bases, such as LiOH, NaOH, $Ca(OH)_2$, $K_2CO_3$, $Na_2CO_3$, $Mg(OH)_2$, $MgCO_3$, or organic bases such as amine bases, in particular primary, secondary or tertiary amine bases, in particular the ones mentioned above.

Preferred embodiments of compound (VIII) are also preferred for compound (VIII'). In particular the following stereochemistry is preferred:

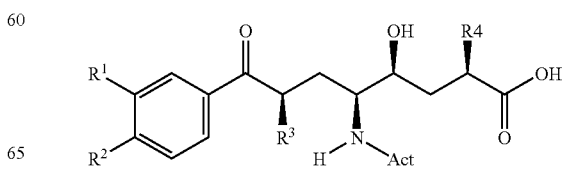

or preferably a salt thereof, in particular as described herein. Preferably, the compound has the following formula

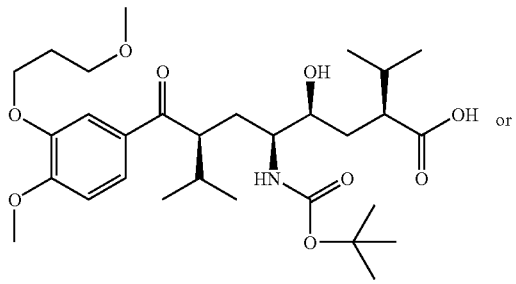

or

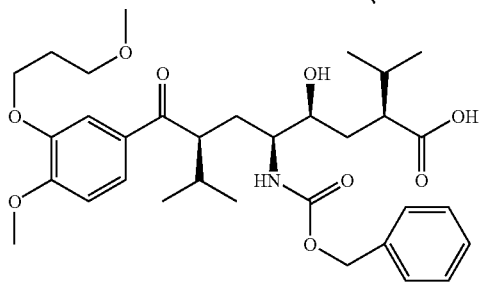

or preferably a salt thereof, in particular as described herein.

In a preferred further embodiment of the invention, this synthesis comprises as a further step or as an individual synthesis the preparation a compound of formula (IX)

(IX)

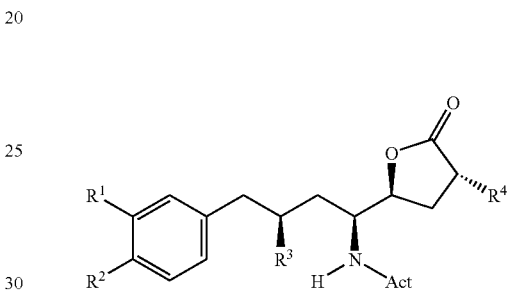

wherein $R^3$ and $R^4$ are as defined for a compound of formula (II), $R^1$ and $R^2$ are as defined for a compound of formula (VIII) and Act is an activating group selected from an amino protecting group, in particular a carbamate, or a salt thereof, comprising reduction of the benzylic carbonyl of the compound of formula (VII) as defined above to a methylene moiety. This process step as such, also forms an embodiment of the invention. Similarly, this reaction can be performed by using the compound of formula (VIII') or a salt thereof as the starting material.

Preferred embodiments for $R^3$, $R^4$ and Act can be taken from the definitions for compounds of formula (VI) and preferred embodiments for $R^1$ and $R^2$ can be taken from the definitions for compounds of formula (VIII). Preferably, the compound according to the formula (IX)

has the following stereochemistry:

The reduction to the C8 methylene moiety can be achieved by various means. Typically, hydrogenation and/or reduction with a hydride can be employed and whenever the term "reduction" is used in general terms in this application, it embraces both a hydrogenation and a reduction with a hydride. Possible conversions and intermediates are shown in Scheme 2. Each process step as such as well as the respective intermediates also form an embodiment of the invention.

Scheme 2: Routes to compound of formula (IX)

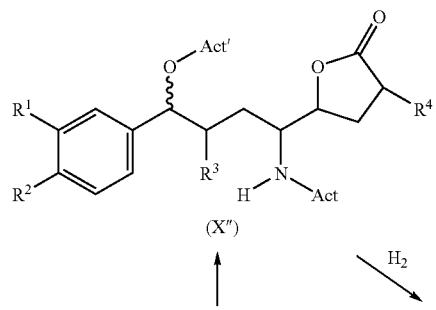

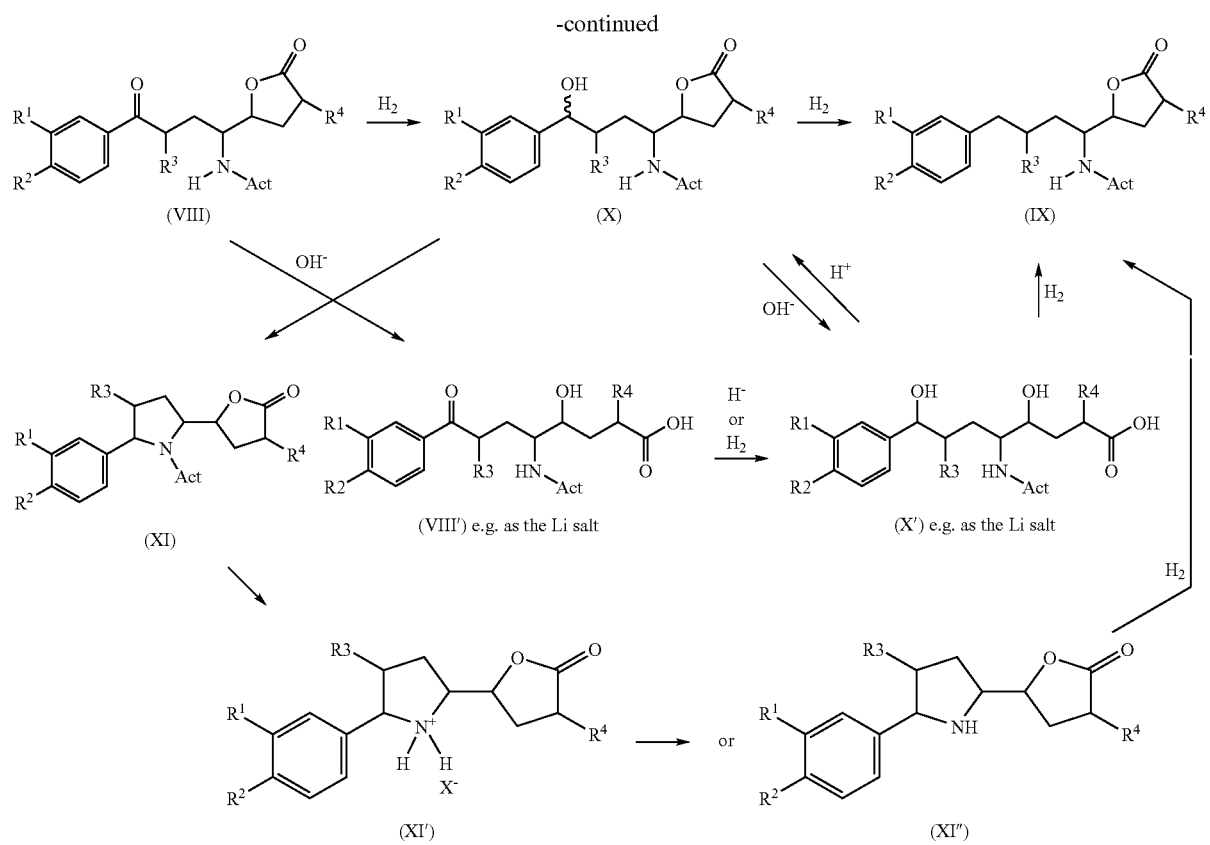

The reduction to compound (IX) can proceed either in a single step or in two steps with the corresponding alcohol (X) as an intermediate (X)

wherein $R^3$ is $C_{1-7}$alkyl or $C_{3-8}$cycloalkyl;

$R^4$ is $C_{1-7}$alkyl, $C_{2-7}$alkenyl, $C_{3-8}$cycloalkyl, phenyl- or naphthyl-$C_{1-4}$alkyl each unsubstituted or mono-, di- or tri-substituted by $C_{1-4}$alkyl, O—$C_{1-4}$alkyl, OH, $C_{1-4}$alkylamino, di-$C_{1-4}$alkylamino, halogen and/or by trifluoromethyl;

$R^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl;

$R^2$ is halogen, hydroxyl, $C_{1-4}$alkyl or $C_{1-4}$alkoxy; and

Act is an activating group selected from an amino protecting group, in particular a carbamate; or a salt thereof.

Compounds of formula (X) were found to be important reactants in the above conversion and, thus, the synthesis of renin inhibitors. Therefore, one aspect of the present invention also is directed to compounds of formula (X). Preferred embodiments are the same as for compound (VIII). The alcohol functionality is typically epimeric and both epimers can be isolated. Preferably, the compound according to the formula (X) has the following stereochemistry:

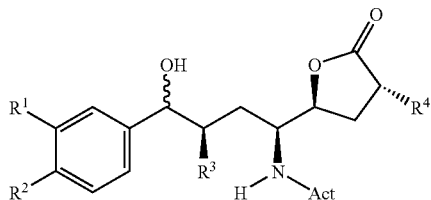

Most preferably, compounds of formula (X) have the following structure:

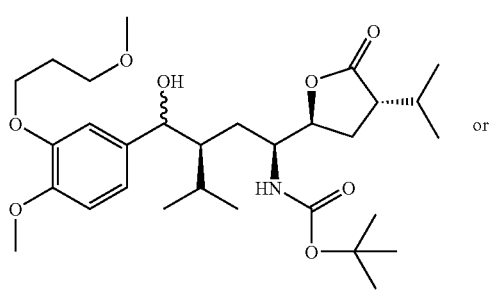

-continued

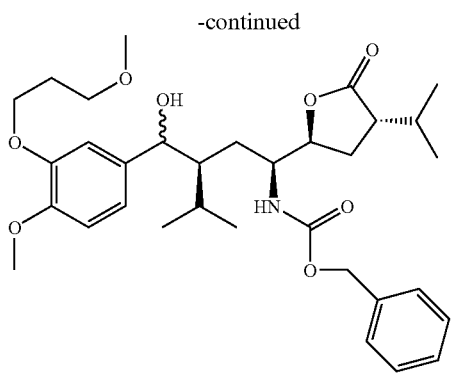

When employing the single step method, the reaction also proceeds via the alcohol (X) which can be isolated. This reaction to convert the carbonyl moiety to a methylene function in position 8 preferably takes place under conditions so as to keep the other functionalities on the molecule intact, in particular the group Act. The conversion to the methylene moiety takes place typically by hydrogenation. Hydrogenation typically takes place in the presence of a catalyst selected from a heterogeneous catalyst or a homogeneous catalyst, such as Wilkinson's catalyst, but preferably a heterogeneous catalyst. Examples of the catalyst include Raney nickel, palladium/C, Pd(OH)$_2$ (Perlman's catalyst), nickel boride, platinum metal or platinum metal oxide, rhodium complexes, ruthenium complexes and zinc oxide, more preferably palladium/C, platinum metal or platinum metal oxide, or Raney nickel, most preferably palladium/C. The catalyst is preferably used in an amount of 1 to 20%, more preferably 5 to 10%. The reaction can be conducted at atmospheric or elevated pressure, such as a pressure of 2-10 bar, e.g. 5 bar, more preferably the reaction is conducted at elevated pressure. The hydrogenation takes place preferably in an inert solvent, more preferably in tetrahydrofuran, toluene, methanol, ethanol and also mixtures of this solvents with water are possible. The reaction time and the temperature are chosen so as to bring the reaction to completion at a minimum time without the production of unwanted side products. Typically the reaction can be conducted at 0° C. to reflux, preferably 0 to 100° C., more preferably 15-70° C., such 30-60° C., for 60 min to 12 h, such as 2 h to 6 h. Longer reaction times may also be appropriate to ensure complete conversion, such as 8 to 24 h.

Alternatively the carbonyl moiety may be first converted to an alcohol (X) by reduction with a complex hydride and then subjected to further reduction (hydrogenolysis) to obtain a compound of formula (IX).

The reduction to an alcohol preferably takes place under conditions so as to keep the other functionalities on the molecule intact, in particular the Act group and the lactone moiety. ee Lit.: M. Larcheveque, et al., J.C.S. Chem. Commun., 83 (1985). Such a reaction is well known to a person skilled in the art and is described e.g. in Methoden der organischen Chemie" (*Methods of Organic Chemistry*), Houben Weyl, 4th edition, Volume IV/c, Reduction I & II. Georg Thieme Verlag, Stuttgart 1974, pp. 1-486 all of which are incorporated herein by reference.

a) R. L. Augustine, "Reduktion", Marcel Dekker, Inc., New York, 1968, 1-94, b) F. Zymalkowski, "Katalytische Hydrierungen", Ferdinand Enke Verlag, Stuttgart, 1965, pp. 103-114, 121-125, 126-144 c) O. H. Wheeler, in "Chemistry of the carbonyl group", Ed. S. Patai, Interscience, New York, 1966, Chapt. 11.

d) R. H. Mitchell et al., Tetrahedron Lett., 21, 2637 (1980);

e) R. T. Blickenstaff et al., Tetrahedron, 24, 2495 (1968);

The reduction typically takes place in the presence of a suitable reducing agent selected from L-Selectride, lithium trialkoxyaluminium hydrides, for example, lithium tri-tert-butyloxy aluminium hydride, lithium triethylborohydride (super Hydride®), lithium tri-sec. butyl boro-hydride) or lithium tri n-butyl borohydride (Lit.: A.-M. Faucher et al., Tetrahedr. Let., 39, 8425 (1998), and M. Larcheveque et al., J.C.S. Chem. Commun., 83 (1985)), or lithium tri-tert.-butoxy aluminium hydride, tetraalkyl-ammoniumborohydrides, Zn(BH$_4$)$_2$ and NaBH$_4$ or by addition of a Lewis acid like CeCl$_3$ to the NaBH$_4$. The reduction takes place preferably in an inert solvent, more preferably in tetrahydrofuran, dichloromethane or toluene or in mixtures of this solvents or in THF/water or ethanol/water (in the case of water soluble substrates with NaBH$_4$ or tetraalkylammonium borohxdride). Lit.: Fieser & Fieser, Vol. XII, page 441, and other volumes. The reaction time and the temperature are chosen so as to bring the reaction to completion at a minimum time without the production of unwanted side products. Typically the reaction can be conducted at 0° C. to reflux, preferably 10 to 100° C., more preferably 20 to 80° C., such as 30-60° C., for 1 to 48 h, preferably 2 h to 12 h, most preferably 3 h to 6 h.

As the next step, the alcohol (X) is further reduced to a compound of formula (IX). This conversion to the methylene moiety takes place typically by hydrogenation. Hydrogenation typically takes place in the presence of a catalyst selected from a heterogeneous catalyst or a homogeneous catalyst, such as Wilkinson's catalyst, preferably a heterogeneous catalyst. Examples of the catalyst include Raney nickel, palladium/C, Pd(OH)$_2$ (Perlman's catalyst), nickel boride, platinum metal or platinum metal oxide, rhodium, ruthenium and zinc oxide, more preferably palladium/C, platinum metal or platinum metal oxide, most preferably palladium/C. The catalyst is preferably used in an amount of 1 to 20%, more preferably 5 to 10%. The reaction can be conducted at atmospheric or elevated pressure, such as a pressure of 2-10 bar, e.g. 5 bar, more preferably the reaction is conducted at elevated pressure. The hydrogenation takes place preferably in an inert solvent, more preferably in tetrahydrofuran, ethyl acetate, toluene, methanol, ethanol, isopropanol and also mixtures of this solvents with water are possible. The reaction time and the temperature are chosen so as to bring the reaction to completion at a minimum time without the production of unwanted side products. Typically the reaction can be conducted at 0° C. to reflux, preferably 0 to 100° C., more preferably 15-70° C., such 30-60° C., for 6 h to 48 h, preferably 10 h to 36 h, most preferably 12 h to 24 h, such as 20-24 h.

The reduction to compound (IX) can also proceed with the corresponding compound (VIII') as a starting material as described above, in particular in the form of a salt such as a Li salt. Preferred embodiments are as described above. In a similar manner as disclosed above, this reaction may proceed in a single step or via the corresponding alcohol (X') as an intermediate

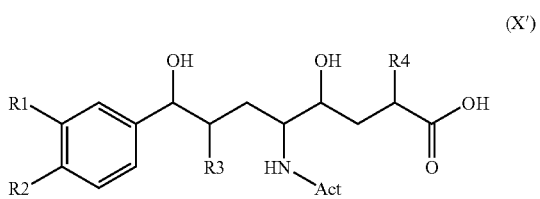

wherein $R^3$ is $C_{1-7}$alkyl or $C_{3-8}$cycloalkyl;

$R^4$ is $C_{1-7}$alkyl, $C_{2-7}$alkenyl, $C_{3-8}$cycloalkyl, phenyl- or naphthyl-$C_{1-4}$alkyl each unsubstituted or mono-, di- or tri-substituted by $C_{1-4}$alkyl, O—$C_{1-4}$alkyl, OH, $C_{1-4}$alkylamino, di-$C_{1-4}$alkylamino, halogen and/or by trifluoromethyl;

$R^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl;

$R^2$ is halogen, hydroxyl, $C_{1-4}$alkyl or $C_{1-4}$alkoxy; and

Act is an activating group selected from an amino protecting group, in particular a carbamate; or a salt thereof.

The conversion of a compound of formula (VIII') to a compound of formula (X') can proceed according to the methods and conditions as disclosed for a compound of formula (VIII) above as the starting material. Preferably the reduction is performed with a hydride source under standard conditions. Examples of the hydride source include NaBH$_4$, LiAlH$_4$, LiBH$_4$, Ca(BH$_4$)$_2$. Reference is made to the literature cites above. Particularly preferred are complex hydrides. These are typically hydride reagents such as the ones mentioned above, in particular NaBH$_4$ or LiAlH$_4$, with chiral ligands such as BINOLs, amino acids, chiral amino alcohols, and other chiral ligands which can form complexes with any of the above hydride reagents. For the preferred procedures and conditions, it is referred to:

1) Org. Proc. Res.& Dev., 4, (2), 107 (2000)
2) Heteroatom Chemistry, 14, (7), 603 (2003)
3) Synth. Commun., 34, 1359, (2004)
4) J. Org. Chem., 61 (24), 8586, (1996)
5) J. Org. Chem., 67, (26), 9186, (2002)
6) Synthesis, (2), 217 (2004) and the literature cited therein, all of which are incorporated herein by reference.

The two epimers (syn and anti with respect to the OH group and R3) may show different reactivity. Especially, it was found that the anti-epimer is much more reactive in the desired hydrogenolytic cleavage of the benzylic OH bond with hydrogen and a catalyst such as Pd/C.

Compounds of formula (X') were found to be important reactants in the above conversion and, thus, the synthesis of renin inhibitors. Therefore, one aspect of the present invention also is directed to compounds of formula (X'). Preferred embodiments are the same as for compound (VIII'). In particular, it is preferred that the compound of the formula (X') is in a salt form as described for the compound of formula (VIII'). The alcohol functionality is typically epimeric and both epimers can be isolated. Preferably, the compound according to the formula (X') has the following stereochemistry:

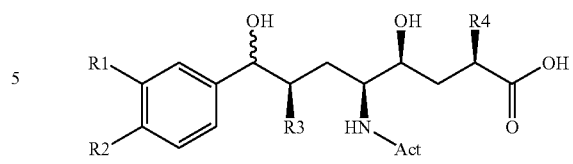

or preferably a salt thereof, in particular as described herein for the compound of formula (VIII'). Most preferably, compounds of formula (X') have the following structure:

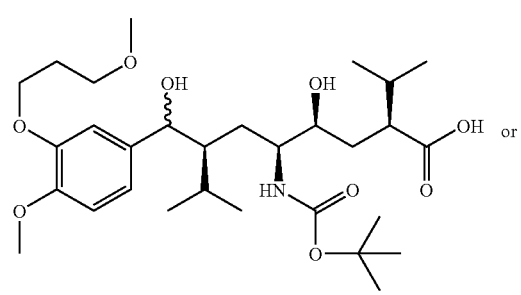

syn and anti

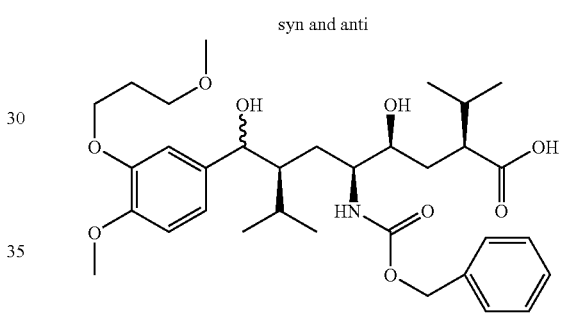

syn and anti or preferably a salt thereof, in particular as described herein for the compound of formula (VIII').

The conversion of a compound of formula (X') to a compound of formula (IX) can proceed according to the methods and conditions as disclosed for a compound of formula (X) above as the starting material.

Instead of further reducing the compound of formula (X) directly to the compound of formula (IX), the compound of formula (X) may be alternatively cyclised to a pyrrolidine compound of formula (XI) as shown in Scheme 2:

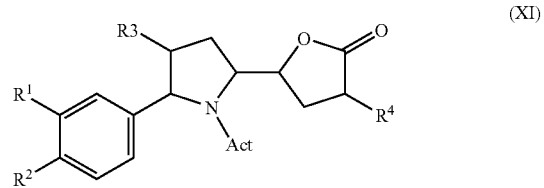

wherein $R^3$ is $C_{1-7}$alkyl or $C_{3-8}$cycloalkyl;

$R^4$ is $C_{1-7}$alkyl, $C_{2-7}$alkenyl, $C_{3-8}$cycloalkyl, phenyl- or naphthyl-$C_{1-14}$alkyl each unsubstituted or mono-, di- or tri-substituted by $C_{1-4}$alkyl, O—$C_{1-4}$alkyl, OH, $C_{1-4}$alkylamino, di-$C_{1-4}$alkylamino, halogen and/or by trifluoromethyl;

$R^1$ is halogen, hydroxyl, $C_{1-6}$halogenalkyl, $C_{1-6}$alkoxy-$C_{1-6}$ alkyloxy or $C_{1-6}$alkoxy-$C_{1-6}$alkyl;

$R^2$ is halogen, hydroxyl, $C_{1-4}$alkyl or $C_{1-4}$alkoxy; and

Act is an activating group selected from an amino protecting group, in particular a carbamate; or a salt thereof.

Preferred embodiments are the same as for compound (VIII).

Thus in a preferred further embodiment of the invention, this synthesis comprises as a further step or as an individual synthesis the preparation a compound of formula (XI)

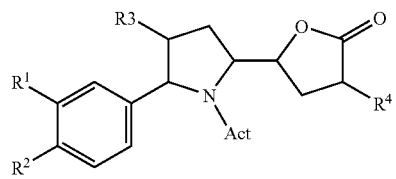

(XI)

wherein $R^3$, $R^4$, $R^1$, $R^2$ and Act are as defined above, or a salt thereof, comprising cyclisation of the benzylic alcohol and the amine moieties of the compound of formula (X) as defined above to a pyrrolidine moiety. This process step as such, also forms an embodiment of the invention.

Preferred embodiments for $R^3$, $R^4$ and Act can be taken from the definitions for compounds of formula (VI) and preferred embodiments for $R^1$ and $R^2$ can be taken from the definitions for compounds of formula (VIII).

The reaction of the compound of the formula (X) to form the pyrrolidine of formula (XI) preferably takes place under conditions so as to keep the other functionalities on the molecule intact. It is considered that during the reaction protonation of the benzylic alcohol occurs followed by elimination of water to give a benzylic carbocation which is trapped intramolecularly by the nitrogen atom, connected with an Act group such as a Boc-group or a Cbz-group which is stable under these conditions. The cyclisation is typically effected under acidic conditions. Suitable acids include strong organic or inorganic acids or acidic ion exchange resins. A suitable strong acid should preferably possess a pKa of <4.75. Preferred are organic acids such as tartaric acid and oxalic acid, or aryl or alkyl sulfonic acids, mineral acids such as phosphoric acid or phosphonic acid, or acidic ion exchange resins such as Amberlyst or Dowex, such as Dowex 50WX2-100, 50WX2-200, 50WX2-400, more preferably the reaction is conducted with an acidic ion exchange resin. When using an organic or inorganic acid the reaction is preferably conducted under anhydrous conditions. The reaction can be conducted in any suitable solvent, preferably an inert solvent such as an aromatic or a halogenated solvent, more preferably methylene chloride or toluene. The reaction time and the temperature are chosen so as to bring the reaction to completion at a minimum time without the production of unwanted side products. Typically the reaction can be conducted at 0° C. to reflux, preferably 10 to 40° C., more preferably 15-30° C., such as room temperature, for 1 min to 12 h, preferably 10 min to 6 h, most preferably 30 min to 4 h, such as 2 to 3 h.

The pyrrolidine of formula (XI) is then in another preferred embodiment of the present invention converted to the compound of formula (IX) by reduction or hydrogenation. Thus in a preferred further embodiment of the invention, this synthesis comprises as a further step or as an individual synthesis the preparation of a compound of formula (IX)

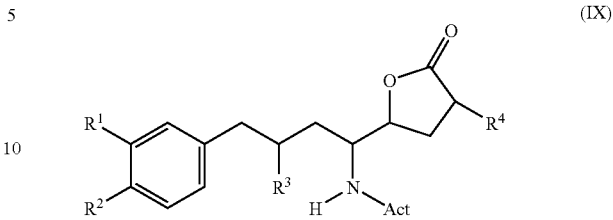

(IX)

wherein $R^3$, $R^4$, $R^1$, $R^2$ and Act are as defined above, or a salt thereof, comprising hydrogenation or reduction of the pyrrolidine moiety of the compound of formula (XI) as defined above to ring-open and to obtain the methylene moiety in position 8. This process step as such, also forms an embodiment of the invention.

The conversion to compound (IX) from compound (XI) can proceed either in a single step or in two or more steps with the corresponding pyrrolidine salt (XI') or the pyrrolidine free base (XI") as an intermediate (see Scheme 2).

When conducting the conversion as a single step, the reaction preferably utilizes metal initiated reduction. Typical metals employed are alkaline or alkaline earth metals, preferably Li, Na, or Ca. Such reductions are typically conducted in liquid ammonia or similar reaction conditions like lower alkyl alcohols or lower alkyl amines as known to the person skilled in the art and as described e.g. Houben-Weyl, Vol. XI/1, page 968-975, and also Houben-Weyl, Vol. 4/1 c, pp. 645-657, and R. L. Augustine, "Reduktion", Marcel Dekker, Inc., New York, 1968, "dissolving metal reduction", which are incorporated herein by reference.

When obtaining the compound of formula (IX) via the intermediate (XI') or (XI"), the pyrrolidine is preferably subjected to hydrogenation. Hydrogenation typically takes place in the presence of a catalyst selected from a heterogeneous catalyst. Examples of the catalyst include Raney nickel, palladium/C, Pd(OH)$_2$ (Perlman's catalyst), nickel boride, platinum metal or platinum metal oxide, rhodium, ruthenium and zinc oxide, more preferably palladium/C, platinum metal or platinum metal oxide, most preferably palladium/C. The catalyst is preferably used in an amount of 1 to 20%, more preferably 5 to 10%. The reaction can be conducted at atmospheric or elevated pressure, such as a pressure of 2-10 bar, e.g. 5 bar, more preferably the reaction is conducted at atmospheric pressure. The hydrogenation takes place preferably in an inert solvent, more preferably in tetrahydrofuran, toluene, alcohols such as methanol, ethanol and also mixtures of these solvents with water are possible, most preferably methanol, ethanol and also mixtures of these solvents with water.

The reaction time and the temperature are chosen so as to bring the reaction to completion at a minimum time without the production of unwanted side products. Typically the reaction can be conducted at 0° C. to reflux, preferably 0 to 100° C., more preferably 15-70° C., such 30-60° C. or room temperature, for 10 min to 12 h, preferably 20 min to 6 h, most preferably 30 min to 4 h, such as 1 to 3 h. For more detail reference is made to Tetrahedron, 54, 1753 (1998). For other methods see also Houben-Weyl, Vol. 4/1c, Reduktion I, page 400-405, and Houben-Weyl, Vol. XI/1, page 968-975, all of which are incorporated herein by reference.

If during this reaction the Act group is split off, it can be re-introduced as described in the preparation of the compound of formula (VI).

Compounds of formula (XI') were found to be important reactants in the above conversion and, thus, the synthesis of renin inhibitors. Therefore, one aspect of the present invention also is directed to compounds of formula (XI'):

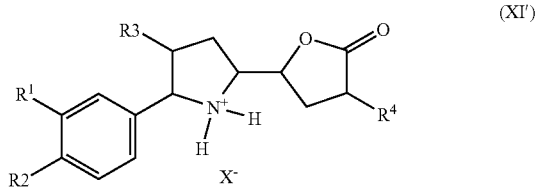

wherein $R^3$ is $C_{1-7}$alkyl or $C_{3-8}$cycloalkyl;

$R^4$ is $C_{1-7}$alkyl, $C_{2-7}$alkenyl, $C_{3-8}$cycloalkyl, phenyl or naphthyl-$C_{1-4}$alkyl each unsubstituted or mono-, di- or tri-substituted by $C_{1-4}$alkyl, O—$C_{1-4}$alkyl, OH, $C_{1-4}$alkylamino, di-$C_{1-4}$alkylamino, halogen and/or by trifluoromethyl;

$R^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl;

$R^2$ is halogen, hydroxyl, $C_{1-4}$alkyl or $C_{1-4}$alkoxy;

and $X^-$ is an anion such as a halide, trifluoroacetate, sulfate, nitrate, oxalate, sulfonate, triflate, phosphonate or phosphate, preferably a halide, trifluoroacetate, sulfonate, phosphonate, phosphate or oxalate.

Preferred embodiments for $R^3$ and $R^4$ can be taken from the definitions for compounds of formula (VI) and preferred embodiments for $R^1$ and $R^2$ can be taken from the definitions for compounds of formula (VIII).

Compounds of formula (XI") were also found to be important reactants in the above conversion and, thus, the synthesis of renin inhibitors. Therefore, one aspect of the present invention also is directed to compounds of formula (XI"):

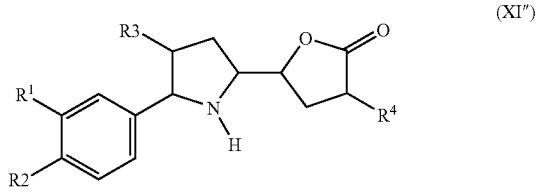

wherein $R^3$ is $C_{1-7}$alkyl or $C_{3-8}$cycloalkyl;

$R^4$ is $C_{1-7}$alkyl, $C_{2-7}$alkenyl, $C_{3-8}$cycloalkyl, phenyl or naphthyl-$C_{1-4}$alkyl each unsubstituted or mono-, di- or tri-substituted by $C_{1-4}$alkyl, O—$C_{1-4}$alkyl, OH, $C_{1-4}$alkylamino, di-$C_{1-4}$alkylamino, halogen and/or by trifluoromethyl;

$R^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl; and $R^2$ is halogen, hydroxyl, $C_{1-4}$alkyl or $C_{1-4}$alkoxy.

Preferred embodiments for $R^3$ and $R^4$ can be taken from the definitions for compounds of formula (VI) and preferred embodiments for $R^1$ and $R^2$ can be taken from the definitions for compounds of formula (VIII).

Instead of further reducing the compound of formula (X) directly to the compound of formula (IX), the compound of formula (X) may be alternatively converted to an activated compound of formula (X"). Thus, in a further embodiment of the present invention, this synthesis comprises as a further step or as an individual synthesis the preparation a compound of formula (X").

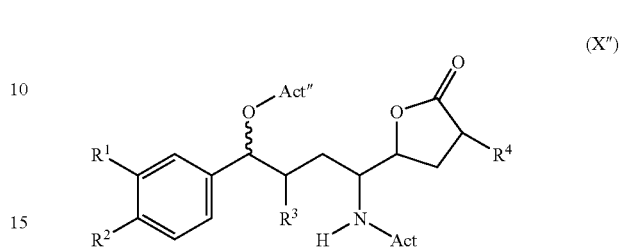

wherein $R^3$ and $R^4$ are as defined for a compound of formula (II), $R^1$ and $R^2$ are as defined for a compound of formula (VIII), Act is an activating group selected from an amino protecting group, in particular a carbamate, and Act" is an electron-withdrawing group, or a salt thereof, comprising conversion of the benzylic alcohol of the compound of formula (X) as defined above to an activated alcohol moiety. This process step as such as well as the compound of formula (X"), also form an embodiment of the invention.

Preferred embodiments for $R^3$, $R^4$ and Act can be taken from the definitions for compounds of formula (VI) and preferred embodiments for $R^1$ and $R^2$ can be taken from the definitions for compounds of formula (VIII).

The activating group Act" should be an electron withdrawing group according to literature (F. J. McQuillin, et al., J.C.S., (C), 136 (1967) and Houben-Weyl, Vol. 4/1c, pp 73, 379-383. For example trifluoracetyl, or similar electron withdrawing groups. Such electron withdrawing groups like —CO—CF$_3$, or —CO—C$_n$F$_m$, wherein Cn stands for a saturated carbon chain of 2 to 8 and m is 1 to 12, enhance the hydrogenolytic cleavage of benzylic carbon-oxygen bonds by a factor 30-70 or more compared to nonactivated benzylic OH-groups. Therefore an Act"-group should be of the type Act"=—(C=O)—R$^9$, where R$^9$ can be substituted alkyl, alkyl-oxy-R$^{10}$, aralkyl, aryl, substituted aryl (especially subst. with EWG-substituents such as F, CF$_3$, NO$_2$ or SO$_2$alkyl or SO$_2$aryl.), O-alkyl, O-aryl, NH—R$^{10}$ (where R$^{10}$ can be alkyl, aryl, aralkyl, benzyl, benzoyl, subst. sulfonyl. In all cases an EWG moiety, such as one or more F or CF$_3$, should be part of these residues.

The attachment of an activating group like Act" can be achieved by reacting compounds of type (X) in an aprotic, inert solvent like toluene, THF, TBME, EtOAc, di-chloromethane, etc. with an acid halide or a symmetrical anhydride of the above mentioned carboxylic acids or mixed anhydrides with other acids, or phosgene derivatives, or carbonates, or isocyanates, or benzoylisocyantes or sulfonylisocyanates.

The compounds of formula (X") can then be converted to the compounds of formula (IX). Thus in a preferred further embodiment of the invention, this synthesis comprises as a further step or as an individual synthesis the preparation of a compound of formula (IX)

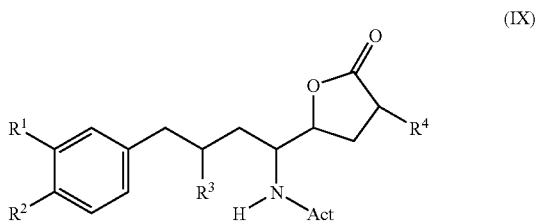

(IX)

wherein $R^3$, $R^4$, $R^1$, $R^2$ and Act are as defined above, or a salt thereof, comprising hydrogenation or reduction of the activated alcohol moiety of the compound of formula (X″) as defined above to obtain the methylene moiety in position 8. This process step as such, also forms an embodiment of the invention.

The process conditions can be chosen in a similar manner as for the conversion of compound of formula (X) to a compound of formula (IX).

As a further alternative approach, the compound of formula (X) may be subjected to radical-based de-oxygenation (reduction) to yield the compound of formula (IX). Radical based reductions are less prone to stereochemical differentiation, since usually a planar carbon radical intermediate is generated, which is reduced by recombination with a hydrogen radical. This leads to similar reducibility of both epimers of the compound of formula (X) in this case.

Thus, in an alternative embodiment of the invention, this synthesis comprises as a further step or as an individual synthesis the preparation a compound of formula (IX)

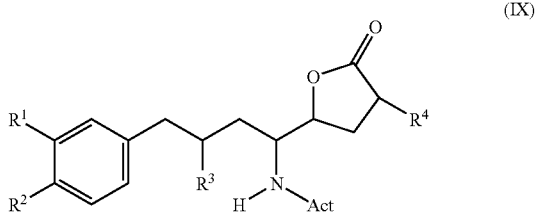

(IX)

wherein $R^3$ and $R^4$ are as defined for a compound of formula (II) and Act is an activating group selected from an amino protecting group, in particular a carbamate, $R^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl; $R^2$ is halogen, hydroxyl, $C_{1-4}$alkyl or $C_{1-4}$alkoxy, or a salt thereof;

comprising transformation of the compound of formula (X) as defined herein to a thiocarbonyl derivative and subsequently subjecting same to radical-based reduction to obtain the compound of formula (IX). This process step as such also forms an embodiment of the invention.

The thiocarbonyl derivative can be any known thiocarbonyl derivative known in the art suitable for radical-based de-oxygenation. Preferred examples are thionocarbamates, such as imidazolyl derivatives, thiocarbonyls, such as xanthates, or thionocarbonates. Particularly preferred is a thionocabamate of formula (XV)

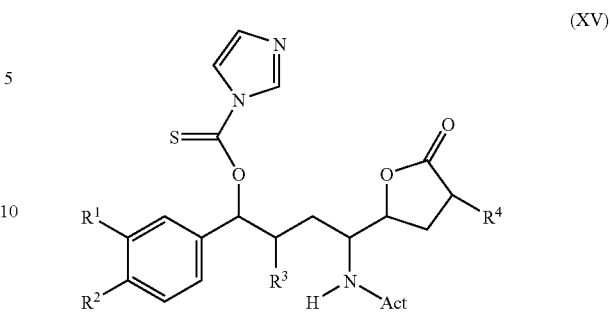

(XV)

wherein $R^3$ and $R^4$ are as defined for a compound of formula (II) and Act is an activating group selected from an amino protecting group, in particular a carbamate, $R^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl; $R^2$ is halogen, hydroxyl, $C_{1-4}$alkyl or $C_{1-4}$alkoxy, or a salt thereof.

Compounds of formula (XV), were found to be important reactants in the above conversion and, thus, the synthesis of renin inhibitors. Therefore, one aspect of the present invention also is directed to compounds of formula (XV). Preferred embodiments are the same as for compound (VIII). The alcohol functionality is typically epimeric and both epimers can be isolated. Preferably, the compound according to the formula (XV) has the following stereochemistry:

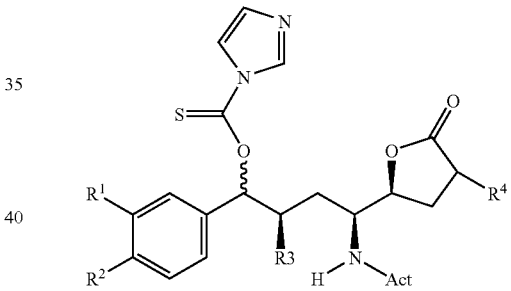

For the transformation of the benzylic alcohol to the thioncarbonyl derivative, methods known in the art may be employed. For thionocarbamates, in particular the compound of formula (XV) see e.g. the methods as described in Derek H. R. Barton and Stuart W. McCombie, *J. Chem. Soc., Perkin Trans.* 1, 1975, 1574, for thiocarbonyls such as xanthates see e.g. Derek H. R. Barton, Doo Ok Jang, Joseph Cs. Jaszberenyi, *Tetrahedron Letters* 1990, 31, 3991; for thinocarbonates see e.g. M. J. Robins, J. S. Wilson, *J. Am. Chem. Soc.* 1981, 103, 933 and M. J. Robins, J. S. Wilson, *J. Am. Chem. Soc.* 1983, 105, 4059.

The radical-based de-oxygenation is performed using standard methodology, in particular Barton.McCombie conditions as forth in the literature references for the thiocarbonyl derivative formation. It is preferred to use either $Bu_3SnH$ or tris(trimethylsilyl)-silane as a reducing agent. When tris(trimethylsilyl)silane is used as reducing agent, a tertiary thiol such as dodecyl-mercaptane is added as catalyst. For conditions using the tris(trimethylsilyl)-silane see e.g. Dietmar Schummer, Gerhard Höfle, *Synlett.* 1990, 705. Alternatively, catalytic amounts of $Bu_3SnBH$ in the presence of another reducing agent, e.g. $NaBH_4$ can be employed. Other silanes e.g. phenylsilane, diphenylsilane and triphenylsilane are also useful for the reduction step, see e.g. D. H. R. Barton, P. Blundell, J. Dorchak, D. O. Jang and, J. Cs. Jaszberenyi, *Tetrahedron* 1991, 47, 8969; D. H. Barton, D. O. Jang, J. Cs. Jaszberenyi, *Tetrahedron* 1993, 49, 7193. Additional reducing agents, which have been used in radical based deoxygenations in the literature, such as dialkyl phosphites, hypophosphorous acid and its salts, see e.g. T. Sato, H. Koga, K. Tsuzuki, *Heterocycles* 1996, 42, 499, as well as 2-propanol in the presence of dilauroyl peroxide, see e.g. A. Liard, B. Quicklet-Sire, S. Z. Zard, *Tetrahedron Lett.* 1996, 37, 5877, are also useful to achieve the desired deoxygenation.

It is also possible to directly obtain the compound of formula (X) from a compound of formula (VI) without isolation of any intermediates as a one-pot-synthesis. Thus, in a preferred alternative embodiment of the invention, this synthesis comprises as a further step or as an individual synthesis the preparation a compound of formula (X)

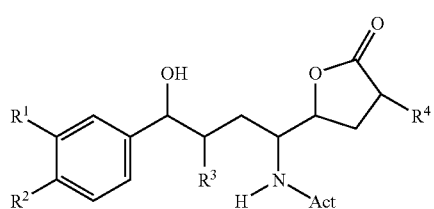
(X)

wherein $R^3$ and $R^4$ are as defined for a compound of formula (II) and Act is an activating group selected from an amino protecting group, in particular a carbamate, $R^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl; $R^2$ is halogen, hydroxyl, $C_{1-4}$alkyl or $C_{1-4}$alkoxy, or a salt thereof;

comprising the step of lactam ring opening of the N-activated lactam lactone of formula (VI) or a salt thereof defined above with a compound of formula (VII)

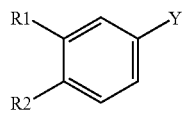
(VII)

wherein Y is a metal containing group such as —Li, —MgX, -magnesates, aryl magnesium species such as

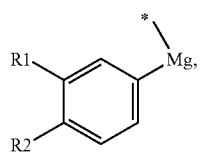

wherein R1 and R2 are as defined herein, alkyl magnesium species, such as branched $C_{1-7}$alkyl-Mg—, —MnX, (alkyl)$_3$MnLi—, or —CeX$_2$ wherein X is halogen such as Cl, I or Br, more preferably Br; and $R^1$ and $R^2$ are as defined for a compound of formula (X) above, to obtain a compound of formula (VIII'), or a salt thereof, as defined above, followed by reduction of the benzylic carbonyl group of the compound of formula (VIII') or a salt thereof to obtain a compound of formula (X'), or a salt thereof, as defined above, and lactonization of the compound of formula (X') to obtain a compound of formula (X).

This process step as such also forms an embodiment of the invention. For this conversion, see also D. Savoia, et al., J. Org. Chem., 54, 228 (1989), and literature cited there.

Preferred embodiments for the compounds of formulas (VI), (VII), (VIII'), (X') and (X) can be taken from the definitions for each of these compounds as defined above. Most preferably both compounds (VIII') and (X') are used in the salt form, in particular as the Li salt.

For the conversion to a compound of formula (VIII') to a compound of formula (X) the same or similar methods as described above individually for each conversion can be employed, namely as described for the conversion from a compound of formula (VI) to a compound of formula (VII) including salt formation to a compound of formula (VIII'), and further conversion to a compound of formula (X'). For this last step in particular the methods as disclosed for the conversion of a compound of formula (VIII') to a compound of formula (X') should be employey, preferably the hydride reduction conditions as mentioned therein including the hydride reagents such as NaBH$_4$ or LiAlH$_4$, and also the complex hydride conditions described therein. The free acid will form the lactone moiety of compound (X), preferably by heating the mixture to e.g. 30 to 80° C., more preferably 40 to 60° C., such as 50° C. Typically, acidic conditions, such as mild acidic conditions as known in the art using e.g. organic acids such as citric acid, are employed for the lactonization.

In a preferred further embodiment of the invention, this synthesis comprises as a further step or as an individual synthesis the preparation a compound of formula (XII)

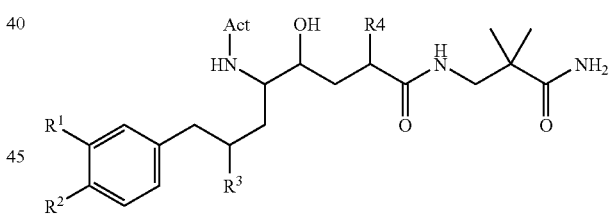
(XII)

wherein $R^3$ and $R^4$ are as defined for a compound of formula (II), $R^1$ and $R^2$ are as defined for a compound of formula (VIII) and Act is an activating group selected from an amino protecting group, in particular a carbamate, or a salt thereof, comprising reacting a compound of the formula (IX) as defined above, or a salt thereof, with an amine of the formula (XIII),

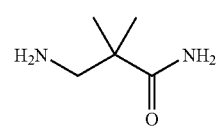
(XIII)

(wherein the amido nitrogen can also be protected if desired and the protecting group then be removed in the corresponding protected compound of the formula XII), or a salt thereof. This process step as such also forms an embodiment of the invention.

This conversion can proceed according to typical peptide coupling reactions well known in the art, e.g. in analogy to the process disclosed in EP-A-678 503 which is incorporated herein by reference, see in particular examples 124 and 131 or as disclosed in WO 02/02508, which is incorporated herein by reference, in particular example H1 on page 35 (preparation of J1).

Preferred embodiments for $R^3$, $R^4$ and Act can be taken from the definitions for compounds of formula (VI) and preferred embodiments for $R^1$ and $R^2$ and Act can be taken from the definitions for compounds of formula (VIII). Preferably, the compound according to the formula (XII) has the following stereochemistry:

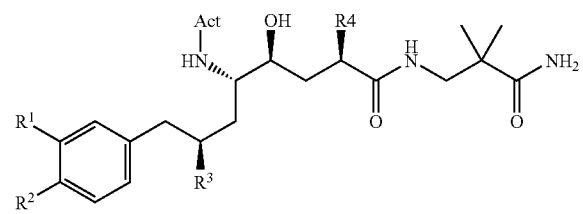

The reaction preferably takes place under standard conditions for the formation of an amide from a lactone, e.g. in an appropriate solvent or solvent mixture, e.g. in an ether, such as tert-butylmethyl ether, preferably in the presence of a bifunctional catalyst with a weak acidic and a weak basic group, e.g. 2-hydroxypyridine or proline, in the presence of an appropriate base, e.g. a tertiary nitrogen base, such as triethylamine, at appropriate temperatures e.g. in the range from 0° C. to the reflux temperature of the reaction mixture, e.g. from 0 to 85° C.

The amide coupling to compound (XII) using a compound of formula (XIII) as described above can also proceed in a similar manner as disclosed above using the ring-opened analogue of a compound of formula (IX). Thus, this reaction may proceed in using the corresponding compound of the formula (IX') as a starting material (IX')

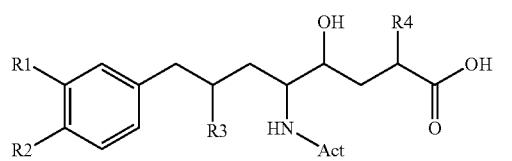

wherein $R^3$ is $C_{1-7}$alkyl or $C_{3-8}$cycloalkyl;

$R^4$ is $C_{1-7}$alkyl, $C_{2-7}$alkenyl, $C_{3-8}$cycloalkyl, phenyl- or naphthyl-$C_{1-4}$alkyl each unsubstituted or mono-, di- or tri-substituted by $C_{1-4}$alkyl, O—$C_{1-4}$alkyl, OH, $C_{1-4}$alkylamino, di-$C_{1-4}$alkylamino, halogen and/or by trifluoromethyl;

$R^1$ is halogen, hydroxyl, $C_{1-6}$halogenalkyl, $C_{1-6}$alkoxy-$C_{1-6}$alkyloxy or $C_{1-6}$alkoxy-$C_{1-6}$alkyl;

$R^2$ is halogen, hydroxyl, $C_{1-4}$alkyl or $C_{1-4}$alkoxy; and

Act is an activating group selected from an amino protecting group, in particular a carbamate; or a salt thereof. This process step as such also forms an embodiment of the invention.

The conversion of a compound of formula (IX) to a compound of formula (IX') can proceed according to the methods and conditions as disclosed for the lactone ring opening of a compound of formula (II) above to a compound of formula (II'). It is recommended to protect the alcohol moiety of the compound of formula (IX') prior to the amide coupling reaction, Standard alcohol protection/deprotection chemistry can be employed.

Compounds of formula (IX') were found to be important reactants in the above conversion and, thus, the synthesis of renin inhibitors. Therefore, one aspect of the present invention also is directed to compounds of formula (IX'). Preferred embodiments are the same as for compound (VIII'). In particular, it is preferred that the compound of the formula (IX') is in a salt form as described for the compound of formula (VIII'). Preferably, the compound according to the formula (X') has the following stereochemistry:

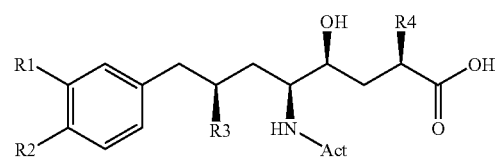

or preferably a salt thereof, in particular as described herein for the compound of formula (VIII'). Most preferably, compounds of formula (IX') have the following structure:

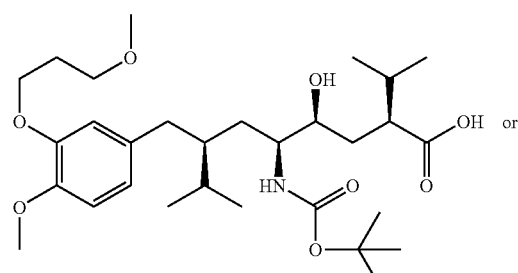

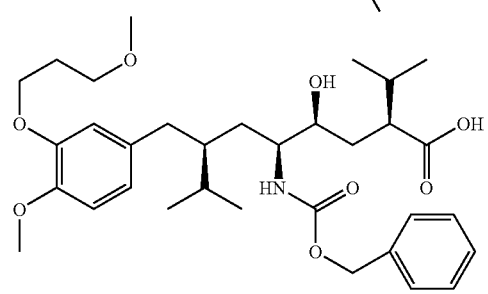

or preferably a salt thereof, in particular as described herein for the compound of formula (VIII').

The conversion of a compound of formula (IX') to a compound of formula (XII) can proceed according to the methods and conditions as disclosed for a compound of formula (IX) above as the starting material.

Compounds of formula (XII) may then be converted into a compound of formula (XIV)

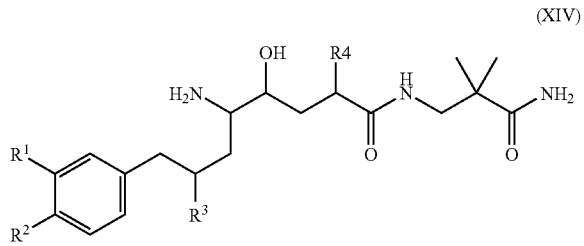

(XIV)

wherein $R^3$ and $R^4$ are as defined for a compound of formula (II), $R^1$ and $R^2$ are as defined for a compound of formula (VIII), or a salt thereof, said conversion comprising removing the activating group Act; and, if desired, converting an obtainable free compound of the formula XIV into a salt (which is preferred) or an obtainable salt into the free compound of the formula XIV or a different salt thereof. For example, if Act is (what is preferred) a $C_1$-$C_7$-alkoxycarbonyl group, such as tert-butoxycarbonyl, the removal can take place under customary conditions, e.g. in the presence of an acid, such as a hydrohalic acid, in an appropriate solvent, such as dioxane, e.g. at temperatures from 0 to 50° C., for example at room temperature. The removal of the group Act is performed using standard protecting group chemistry following the procedures as described in the literature referenced below or using methods well known in the art, see e.g. EP-A-0678 503, which is incorporated herein by reference, in particular example 130, and optionally salt formation using reaction conditions as described e.g. in U.S. Pat. No. 5,559,111, which is incorporated herein by reference, see in particular example 83.

Each of the above mentioned method steps can be used individually in a method to prepare renin inhibitors such as aliskiren. Preferably the steps are used in combination of one or more, most preferably all, to prepare renin inhibitors such as aliskiren.

Preferred embodiments for $R^3$, $R^4$ and Act can be taken from the definitions for compounds of formula (VI) and preferred embodiments for $R^1$ and $R^2$ and Act can be taken from the definitions for compounds of formula (VIII). Most preferably the compound is aliskiren.

All these different synthesis steps and routes show that with compounds of the formula (II) and (VI) highly important new compounds have been found that are central intermediates to a number of possible synthesis routes especially for the synthesis of renin inhibitors such as aliskiren. Therefore, these compounds of the formula (II) and (VI), or a salt thereof, as well as their syntheses form very highly preferred embodiments of the invention.

Listed below are definitions of various terms used to describe the novel intermediates and synthesis steps of the present invention. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

Halo or halogen is preferably fluoro, chloro, bromo or iodo, most preferably fluoro, chloro or bromo; where halo is mentioned, this can mean that one or more (e.g. up to three) halogen atoms are present, e.g. in halo-$C_1$-$C_7$-alkyl, such as trifluoromethyl, 2,2-difluoroethyl or 2,2,2-trifluoroethyl.

Alkyl preferably has up to 20 carbon atom and is more preferably $C_1$-$C_7$-alkyl. Alkyl is straight-chained or branched (one or, if desired and possible, more times). Very preferred is methyl.

Halogenalkyl may be linear or branched and preferably comprise 1 to 4 C atoms, especially 1 or 2 C atoms. Examples are fluoromethyl, difluoromethyl, trifluoromethyl, chloromethyl, dichloromethyl, trichloromethyl, 2-chloroethyl and 2,2,2-trifluoroethyl.

Branched alkyl preferably comprises 3 to 6 C atoms. Examples are i-propyl, i- and t-butyl, and branched isomers of pentyl and hexyl.

Cycloalkyl preferably comprises 3 to 8 ring-carbon atoms, 3 or 5 being especially preferred. Some examples are cyclopropyl, cyclobutyl, cyclopentyl, cyclohexyl and cyclooctyl. The cycloalkyl may optionally be substituted by one or more substituents, such as alkyl, halo, oxo, hydroxy, alkoxy, amino, alkylamino, dialkylamino, thiol, alkylthio, nitro, cyano, heterocyclyl and the like.

Alkenyl may be linear or branched alkyl containing a double bond and comprising preferably 2 to 12 C atoms, 2 to 8 C atoms being especially preferred. Particularly preferred is a linear $C_{2-4}$alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylamino and dialkylamino may be linear or branched. Some examples are methylamino, dimethylamino, ethylamino, and diethylamino.

Alkoxy-alkyloxy may be linear or branched. The alkoxy group preferably comprises 1 to 4 and especially 1 or 2 C atoms, and the alkyloxy group preferably comprises 1 to 4 C atoms. Examples are methoxymethyloxy, 2-methoxyethyloxy, 3-methoxypropyloxy, 4-methoxybutyloxy, 5-methoxypentyloxy, 6-methoxyhexyloxy, ethoxymethyloxy, 2-ethoxyethyloxy, 3-ethoxypropyloxy, 4-ethoxybutyloxy, 5-ethoxypentyloxy, 6-ethoxyhexyloxy, propyloxymethyloxy, butyloxymethyloxy, 2-propyloxyethyloxy and 2-butyloxyethyloxy.

Alkoxyalkyl may be linear or branched. The alkoxy group preferably comprises 1 to 4 and especially 1 or 2 C atoms, and the alkyl group preferably comprises 1 to 4 C atoms. Examples are methoxymethyl, 2-methoxyethyl, 3-methoxypropyl, 4-methoxybutyl, 5-methoxypentyl, 6-methoxyhexyl, ethoxymethyl, 2ethoxyethyl, 3-ethoxypropyl, 4-ethoxybutyl, 5-ethoxypentyl, 6-ethoxyhexyl, propyloxymethyl, butyloxymethyl, 2-propyloxyethyl and 2-butyloxyethyl.

Alkoxy may be linear or branched and preferably comprise 1 to 4 C atoms. Examples are methoxy, ethoxy, n- and i-propyloxy, n-, i- and t-butyloxy, pentyloxy and hexyloxy.

Protecting groups may be present (see also under "General Process Conditions") and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter. Preferably, if two or more protecting groups are present in one intermediate mentioned herein, they are chosen so that, if one of the groups needs to be removed, this can be done selectively, e.g. using two or more different protecting groups that are cleavable under different conditions, e.g. one class by mild hydrolysis, the other by hydrolysis under harder conditions, one class by hydrolysis in the presence of an acid, the other by hydrolysis in the presence of a base, or one class by reductive cleavage (e.g. by catalytic hydrogenation), the other by hydrolysis, or the like.

As hydroxyl protecting group, any group that is appropriate for reversible protection of hydroxy groups is possible, e.g. those mentioned in the standard textbooks under "General Process Conditions". A hydroxyl protecting group may, just to mention a few examples, be selected from a group comprising (especially consisting of a silyl protecting group, especially diaryl-lower alkyl-silyl, such as diphenyl-tert-butylsilyl, or more preferably tri-lower alkylsilyl, such as tert-butyldimethylsilyl or trimethylsilyl; an acyl group, e.g. lower alkanoyl, such as acetyl; benzoyl; lower alkoxycarbonyl, such as tert-butoxycarbonyl (Boc), or phenyl-lower alkoxycarbonyl, such as benzyloxycarbonyl; tetrahydropyranyl; unsubstituted or substituted 1-phenyl-lower alkyl, such as benzyl or p-methoxybenzyl, and methoxymethyl. Boc (selectively removable by hydrolysis) and benzyl (selectively removable by hydrogenation) are especially preferred.

As amino protecting group, any group that is appropriate for reversible protection of hydroxy groups is possible, e.g. those mentioned in the standard textbooks under "General Process Conditions". An amino protecting group may, just to mention a few examples, be selected from a group comprising (especially consisting of) acyl (especially the residue of an organic carbonic acid bound via its carbonyl group or an organic sulfonic acid bound via its sulfonyl group), arylmethyl, etherified mercapto, 2-acyl-lower alk-1-enyl, silyl or N-lower alkylpyrrolidinylidene. Preferred amino-protecting groups are lower alkoxycarbonyl, especially tert-butoxycarbonyl (Boc), phenyl-lower alkoxycarbonyl, such as benzyloxycarbonyl, fluorenyl-lower alkoxycarbonyl, such as fluorenylmethoxycarbonyl, 2-lower alkanoyl-lower alk-1-en-2-yl and lower alkoxycarbonyl-lower alk-1-en-2-yl, with most preference being given to isobutyryl, benzoyl, phenoxyacetyl, 4-tert-butylphenoxyacetyl, N,N-dimethylformamidinyl, N-methylpyrrolidin-2-ylidene or especially tert-butoxycarbonyl.

Unsubstituted or substituted aryl is preferably a mono- or polycyclic, especially monocyclic, bicyclic or tricyclic aryl moiety with 6 to 22 carbon atoms, especially phenyl (very preferred), naphthyl (very preferred), indenyl, fluorenyl, acenapthylenyl, phenylenyl or phenanthryl, and is unsubstituted or substituted by one or more, especially one to three, moieties, preferably independently selected from the group consisting of $C_1$-$C_7$-alkyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycarbonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminocarbonyl, cyano, sulfo, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminosulfonyl and nitro.

Salts are especially the pharmaceutically acceptable salts of compounds of formula XIV or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds of formula XIV or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalenedisulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-di-methylpiperazine.

When a basic group and an acid group are present in the same molecule, a compound of formula XIV or any of the intermediates mentioned herein may also form internal salts.

For isolation or purification purposes of compounds of the formula XIV or in general for any of the intermediates mentioned herein it is also possible to use pharmaceutically unacceptable salts, for example picrates or perchlorates. For therapeutic use, only pharmaceutically acceptable salts or free compounds of the formula XIV are employed (where applicable comprised in pharmaceutical preparations), and these are therefore preferred at least in the case of compounds of the formula XIV.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter, especially to the compound(s) of the formula XIV, is to be understood as referring also to one or more salts thereof or a mixture of a corresponding free compound, intermediate or starting material and one or more salts thereof, each of which is intended to include also any solvate, metabolic precursor such as ester or amide of the compound of formula XIV, or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

Starting materials are especially the compounds of the formula I, III, VII and/or XIII mentioned herein, intermediates are especially compounds of the formula II, II', IV, V, VI, VIII, VIII', IX, IX', X, X', X'', XI, XI', XI'', XII and/or XV.

The invention relates also to methods of synthesis of the intermediates of the formula II, II', IV, V, VI, VIII, VIII', IX, IX', X, X', X'', XI, XI', XI'', XII and/or XV mentioned above from their respective precursors as mentioned above, including methods with the single steps of a sequence leading to a compound of the formula XIV, more than one or all steps of said synthesis and/or pharmaceutically active substances, especially renin inhibitors, most preferably aliskiren, including methods with the single steps of a sequence leading to a compound of the formula XIV, more than one or all steps of said synthesis and/or pharmaceutically active substances, and/or their use in the synthesis of pharmaceutically active compounds, such as renin inhibitors, especially aliskiren.

General Process Conditions

The following, in accordance with the knowledge of a person skilled in the art about possible limitations in the case of single reactions, applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification. Within the scope of this disclosure only a readily removable group that is not a constituent of the particular desired end product of formula XIV is designated a "protecting group", unless the context indicates otherwise. The protection of functional groups by such protecting groups, the protecting groups themselves, and the reactions appropriate for their introduction and removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/1, Georg Thieme Verlag, Stuttgart 1974, in H.-D. Jakubke and H. Jeschkeit, "Aminosauren, Peptide, Proteine" (*Amino acids, Peptides, Proteins*), Verlag Chemie, Weinheim, Deerfield Beach, and Basel 1982, in "Protecting Groups", Philip J. Kocienski, 3rd Edition, Georg Thieme Verlag, Stuttgart, ISBN 3-13-137003-3 and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974, all of which are incorporated herein by reference. A characteristic of protecting groups is that they can be removed readily (i.e. without the occurrence of undesired secondary reactions) for example by solvolysis, reduction, photolysis or alternatively under physiological conditions (e.g. by enzymatic cleavage). Different protecting groups can be selected so that they can be removed selectively at different steps while other protecting groups remain intact. The corresponding alternatives can be selected readily by the person skilled in the art from those given in the standard reference works mentioned above or the description or the Examples given herein.

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about $-100°$ C. to about $190°$ C., preferably from approximately $-80°$ C. to approximately $150°$ C., for example at from $-80$ to $-60°$ C., at room temperature, at from $-20$ to $40°$ C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning. Where required or desired, water-free or absolute solvents can be used.

Where required, the working-up of reaction mixtures, especially in order to isolate desired compounds or intermediates, follows customary procedures and steps, e.g. selected from the group comprising but not limited to extraction, neutralization, crystallization, chromatography, evaporation, drying, filtration, centrifugation and the like.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula XIV which are described as being preferred. Special preference is given to reaction conditions that are identical or analogous to those mentioned in the Examples. The invention relates also to novel starting compounds and intermediates described herein, especially those leading to compounds mentioned as preferred herein.

The invention especially relates to any of the methods described hereinbefore and hereinafter that leads to aliskiren, or a pharmaceutically acceptable salt thereof.

The following Examples serve to illustrate the invention without limiting the scope thereof, while they on the other hand represent preferred embodiments of the reaction steps, intermediates and/or the process of manufacture of aliskiren, or salts thereof.

Where mentioned in the Examples, "boc" stands for tert-butoxycarbonyl.

EXAMPLES

1) Preparation of Lactam Lactone of Formula (II) Via Anhydride

[3-Isopropyl-5-(4-isopropyl-5-oxo-tetrahydro-furan-2-yl)pyrrolidin-2-one] (IIa)

26.45 g (88.9 mmol) of compound IIIa, are dissolved in 150 ml of toluene.

10.35 g (102.3 mmol) of triethylamine are dissolved in 10 ml of toluene and added to the solution of starting material at room temperature. This solution is then cooled down to 0-5° C. At this temperature a solution of 13.97 g isobutyl-chloroformate dissolved in 10 ml of toluene is added over 25 minutes. After 30 min. stirring at 0-5° C. the suspension is allowed to warm up to room temperature.

The reaction vessel is transferred to the hydrogenation station and is hydrogenated there by addition of 5 g Pd/C, 5%, Engelhard 4522. After 21 hours the reaction suspension is then filtered. The filtrate is diluted with 150 ml of water and the organic phase is separated. After washing with water the organic layer is evaporated. The crude material is dissolved at reflux in 40 ml of ethyl acetate and 20 ml of heptane until a clear solution is obtained. The solution is allowed to cool down to room temperature. The crystallization starts almost immediately and was completed by stirring for further 21 hours at 23-25° C. The suspension is cooled down to 0-5° C. and stirring is continued for additional 3 h at this temperature.

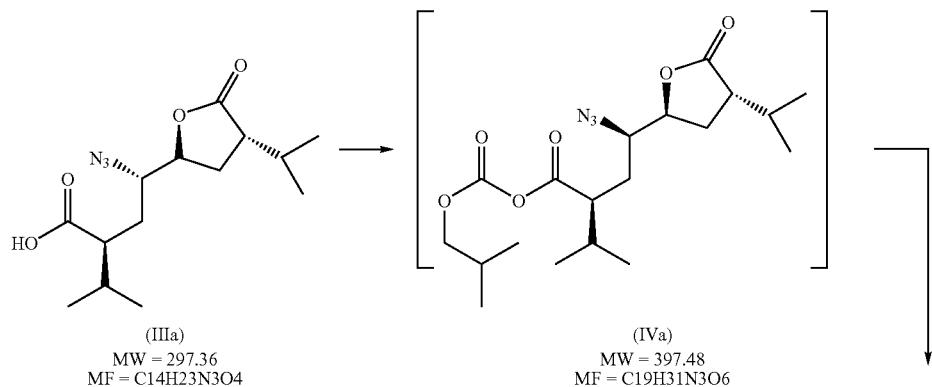

(IIIa)
MW = 297.36
MF = C14H23N3O4

(IVa)
MW = 397.48
MF = C19H31N3O6

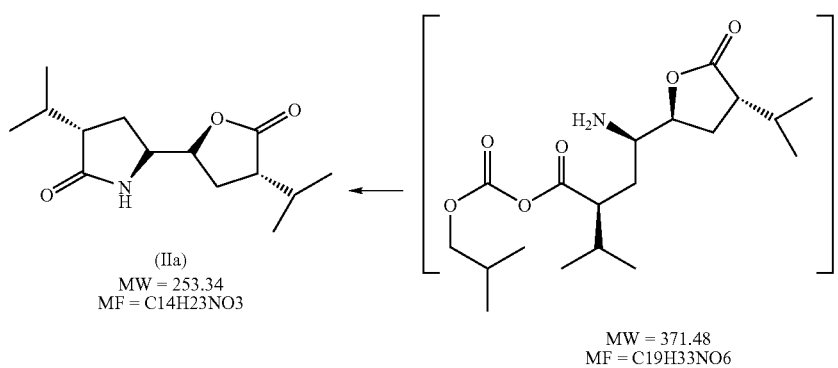

(IIa)
MW = 253.34
MF = C14H23NO3

MW = 371.48
MF = C19H33NO6

After filtration the product IIa is washed with 30 ml of a cold mixture of heptane/ethyl acetate 2:1 and dried under vacuum at 40° C.

A single crystal X-ray determination confirms the absolute configuration at all 4 stereo centers to be (S,S,S,S).

Mp: 136-138° C., clear, colorless $^1$H-NMR (400 MHz, CDCl$_3$): 6.04 (s, 1H), 4.22-4.16 (m, 1H), 3.51-3.46 (m, 1H), 2.55-2.51 (m, 1H), 2.44-2.38 (m, 1H), 2.17-2.09 (m, 3H), 2.07-1.99 (m, 1H), 1.94-1.87 (m, 1H), 1.80-1.73 (m, 1H) 0.99-0.97 (d, 3H), 0.95-0.93 (d, 3H), 0.91-0.89 (d, 3H), 0.85-0.84 (d, 3H)

MS: MH$^+$=254

IR: 1775=Lacton, 1704=Lactam, cm$^{-1}$ (FTIR-Microscopy in transmission)

2) Alternative Preparation of Lactam Lactone of Formula (II) Via Direct Hydrogenation

[3-Isopropyl-5-(4-isopropyl-5-oxo-tetrahydro-furan-2-yl)pyrrolidin-2-one] (IIa)

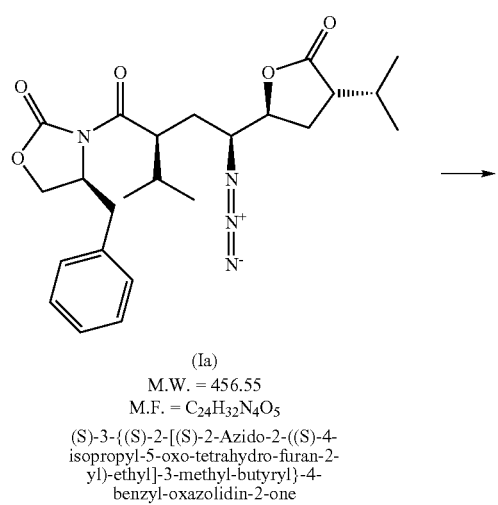

(Ia)
M.W. = 456.55
M.F. = C$_{24}$H$_{32}$N$_4$O$_5$
(S)-3-{(S)-2-[(S)-2-Azido-2-((S)-4-isopropyl-5-oxo-tetrahydro-furan-2-yl)-ethyl]-3-methyl-butyryl}-4-benzyl-oxazolidin-2-one

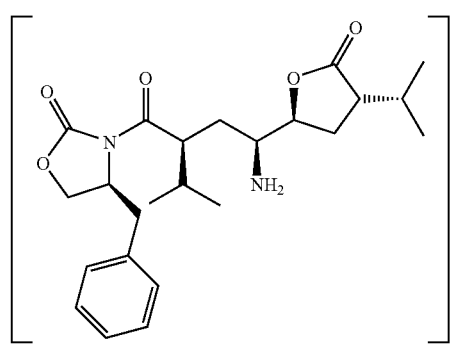

M.W. = 430.55
M.F. = C$_{24}$H$_{34}$N$_2$O$_5$
(S)-3-{(S)-2-[(S)-2-Amino-2-((S)-4-isopropyl-5-oxo-tetrahydro-furan-2-yl)-ethyl]-3-methyl-butyryl}-4-benzyl-oxazolidin-2-one

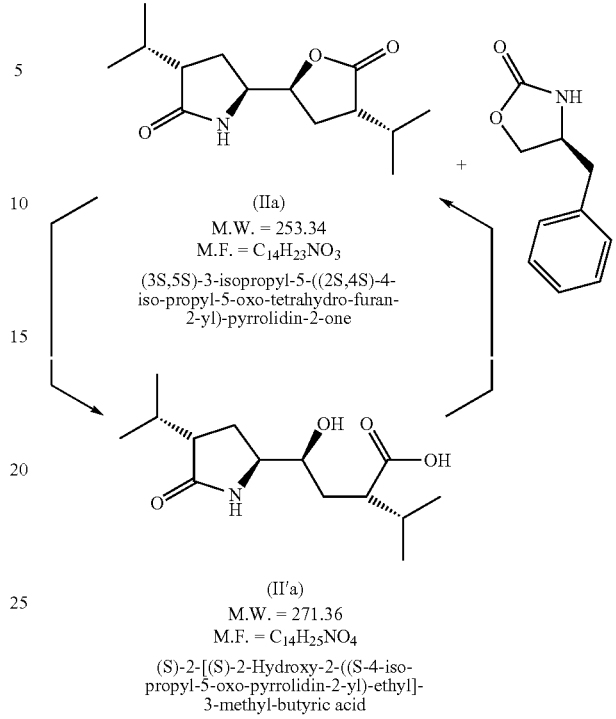

(IIa)
M.W. = 253.34
M.F. = C$_{14}$H$_{23}$NO$_3$
(3S,5S)-3-isopropyl-5-((2S,4S)-4-iso-propyl-5-oxo-tetrahydro-furan-2-yl)-pyrrolidin-2-one (II'a)
M.W. = 271.36
M.F. = C$_{14}$H$_{25}$NO$_4$
(S)-2-[(S)-2-Hydroxy-2-((S-4-iso-propyl-5-oxo-pyrrolidin-2-yl)-ethyl]-3-methyl-butyric acid 9.0 g (19.7 mmol) of compound Ia and 1.08 g of palladium/C (5%) together with 55 ml of toluene are charged to a hydrogenation flask. The hydrogenation is performed at room temperature and normal pressure. After 24 hours the conversion is controlled and is complete. The reaction mixture is filtered through a bed of a filter aid and washed with toluene to remove the catalyst. The toluene is evaporated in vacuum to give a white crystalline solid which consists as a mixture of compound IIa and the Evans auxiliary.

To separate the desired compound IIa from the auxiliary the crystalline solid (9.03 g) is dissolved in 50 ml of toluene. To the resulting clear, colourless solution is added at room temperature 20 ml of 2N sodium hydroxide solution. The resulting emulsion is stirred at room temperature for 1 hour. The desired product is now in the basic aqueous phase as the sodium salt and the auxiliary stays in the toluene phase. The aqueous phase is washed 3-times with 20 ml of toluene to completely extract the auxiliary. The aqueous phase is then acidified with 70 ml of 10% citric acid to adjust the pH to 3. During acidification the lactam hydroxyl acid II'a is precipitated. After stirring for an additional 30 min. the crystals are filtered and dried in vacuum to give a white crystalline powder of compound II'a.

m.p.: 152-155° C.

$^1$H-NMR (DMSO-d$_6$): 0.78 (d, 3H), 0.87-0.91 (3×d, 9H), 1.36 (m, 1H), 1.52 (m, 1H), 1.72-1.85 (cm, 3H), 1.91-1.98 (m, 1H), 2.19-2.24 (m, 1H), 2.33-2.38 (m, 1H), 3.10-3.18 (m, 1H), 3.21-3.25 (m, 1H), 4.73 (broad, 1H, —OH), 7.55 (bs, 1H, NH), 12.03 (broad, 1H, CO$_2$H).

IR: 1730, 1702, 1661, cm$^{-1}$ (FTIR-Microscopy in transmission)

MS: MH$^+$=272

The compound II'a (3.65 g) is then again dissolved in toluene and treated with catalytic amounts of p-toluene sulfonic acid mono hydrate (0.25 g) at 50° C. After 5 h (tlc control) the acid is converted to the desired lactam-lactone IIa. The toluene phase is extracted twice with 50 ml of water and the toluene phase is then evaporated in vacuum to give after drying the white, crystalline compound IIa with a melting point of 136-138° C. The spectroscopic data are identical with the material of example No. 1).

3) Preparation of "Azido Acid" Methylester of Formula (Va)

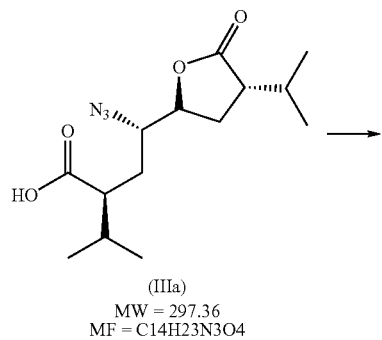

(IIIa)
MW = 297.36
MF = C14H23N3O4

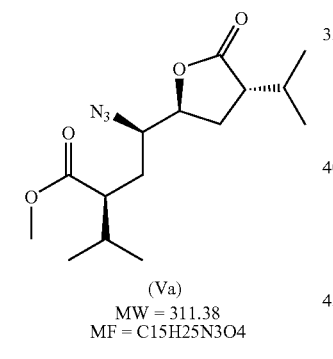

(Va)
MW = 311.38
MF = C15H25N3O4

3.0 g (10.1 mmol) of IIIa are dissolved in 15 ml of dichloromethane at room temperature. 1.66 g (11.1 mmol) 3-methyl-1-p-tolyltriazene is added at room temperature over 25 min. After the addition the reaction solution was allowed to stir at 20-25° C. over a period of 2 hours. During the reaction nitrogen gas is produced. For work up 30 ml of water are added to the solution. The organic phase is washed with 30 ml of 1N HCl (2×15 ml) and 30 ml NaHCO$_3$ 8% (2×15 ml). The organic phase is washed to a neutral pH with 45 ml of water (3×15 ml) and evaporated to yield Va as a yellow oil which crystallizes in the refrigerator.

$^1$H-NMR (400 MHz, CDCL$_3$): 4.40-4.36 (m, 1H), 3.70 (s, 3H), 3.18-3.13 (m, 1H), 2.68-2.62 (m, 1H), 2.52-2.47 (m, 1H), 2.18-2.10 (m, 3H), 1.98-1.93 (q, 1H), 1.89-1.82 (m, 1H), 1.74-1.67 (m, 1H), 1.02-1.00 (d, 3H), 0.94-0.91 (m, 9H)

GC/MS: MH$^+$=312

3b) Hydrogenation of "Azido Acid" Methylester of Formula (Va) to (IIa)

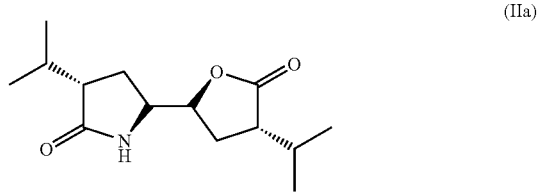

(IIa)

1.5 g of (Va) (4.8 mmol) are dissolved in 15 ml of toluene. 0.3 of Pd/C, (5%), catalyst (Engelhard 4522) are added and hydrogenation is performed at room temperature and normal pressure over 24 hours after which hydrogen uptake was complete. The catalyst is filtered and the filtrate is evaporated in vacuum to give a white powder, which is identical according to $^1$H-NMR, IR and Tlc to compound (IIa).

4) Preparation of Boc-Protected Lactam-Lactone of Formula (VIa)

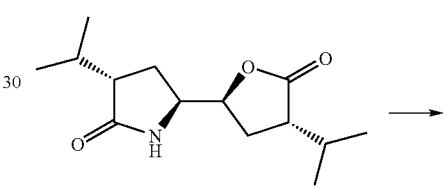

(IIa)

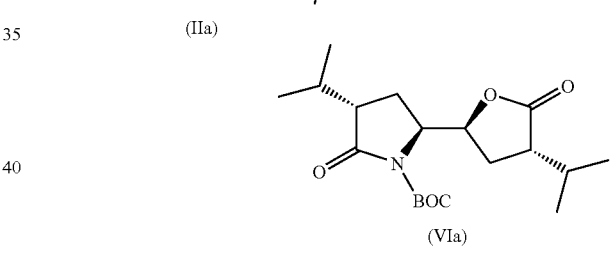

(VIa)

14 g Lactam-lactone IIa (55.3 mmol) and 6.7 mg dimethylamino-pyridine (0.055 mmol) are dissolved together in 100 ml of isopropyl acetate. To this solution is added 5.6 g (55.3 mmol) of triethylamine. This solution is warmed at internal temperature 40-45° C. At this temperature a solution of 13.3 g (60.8 mmol) di-tert-butyl-dicarbonate in 60 ml isopropyl acetate is added over a time of 30 min. The reaction solution is allowed to stir overnight at 40-45° C. After this time the reaction solution is cooled down to room temperature and diluted with 160 ml of heptane. The suspension is then cooled down to 0-5° C. and stirring is continued at this temperature for 5 hours. After filtration the product cake is washed with 50 ml of cold heptane/ethyl acetate and dried under vacuum at 40° C.

$^1$H-NMR (400 MHz, CDCl$_3$): 4.52-4.48 (m, 1H, 4.34-4.29 (m, 1H), 2.68-2.62 (m, 1H), 2.55-2.49 (m, 1H), 2.24-2.08 (m, 4H), 2.03-1.94 (m, 1H), 1.81-1.75 (m, 1H), 1.52 (s, 9H), 1.02-0.98 (pst, 6H), 0.92-0.91 (d, 3H), 0.85-0.84 (d, 3H)

MS: MH$^+$=354

IR: 1777-1760 Lactam/Lacton/Boc, 1185 Boc cm$^{-1}$ (FTIR-Microscopy in transmission)

Mp: 144-145° C., clear, colorless

5) Reaction of Boc-Lactam-Lactone (VIa) with Aryl-Li-Compound (VIIa) to Compound (VIIIa)

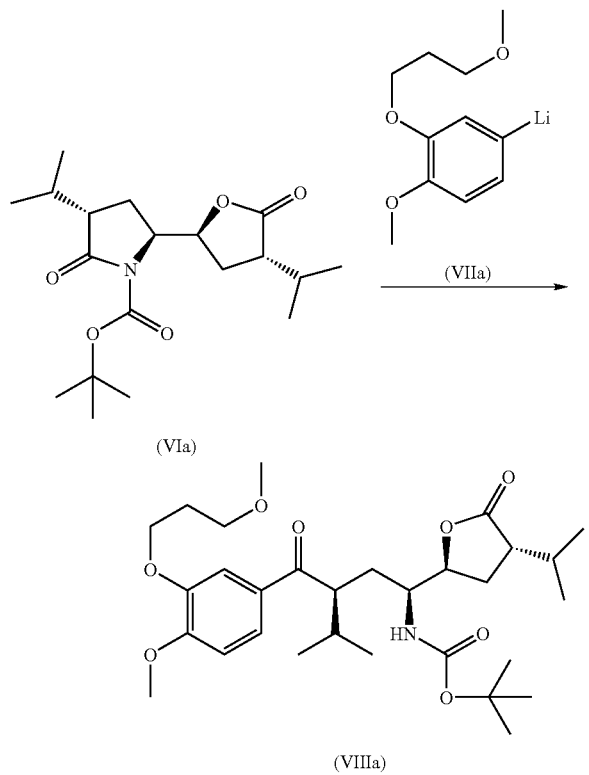

8.56 g (31.12 mmol) aryl bromide (VII'a) are dissolved in 125 ml of THF in a first flask. The solution is cooled at internal temperature of –70° C. To this solution id added over a time of 1 hour 19.8 ml (31.69 mmol) n-butyllithium, 1.6 M solution in hexane. The reaction solution became then a pink-red color. The solution is allowed to stir for 1 hour at –70° C. 10.0 g Boc-lactam-lacton (VIa) (28.29 mmol) are dissolved in 125 ml of dry THF in a second flask. The solution is cooled at internal temperature –50° C. under a stream of argon. To this solution is added the solution of aryl-lithium compound (VIIa) (from flask N° 1) at –55 to –50° C. over a time of 30 minutes.

The reaction mixture is stirred then at –50° C. over 3 hours. The reaction is cooled to a temperature of –70° C. over night.

The next day a second part of aryl-lithium compound is prepared with 1.28 g aryl bromide (VII'a), (4.65 mmol) and 3 ml of n-butyllithium in the same manner as described, and added at internal temperature of –50° C. during a time of 10 minutes to the reaction mixture. The reaction mixture is allowed to stir for 4 hours at –50° C.

For work up the reaction mixture is put on a mixture of 125 ml of toluene and 250 ml of a 10% citric acid solution in water at 0-5° C. during 20 minutes. The quenching is exothermic. The organic phase is washed with 150 ml citric acid, 10% in water, (2×75 ml) and 150 ml NaHCO₃ [8%], (2×75 ml). The organic phase is washed to a neutral pH with 150 ml of water (2×75 ml) and evaporated to yield crude compound (VIIIa) as a nearly white amorphous solid.

To purify the desired compound a part of the solid (6.72 g, 12.22 mmol) is dissolved in 60 ml of ethanol. To the resulting clear colorless solution are added at 0-5° C. 28 ml of 1N lithium hydroxide solution over a time of 20 minutes. This mixture is allowed to warm up to room temperature (21° C.) and stir at this temperature over a period of 1 hour. After this time water and ethanol is partially evaporated and the resulting precipitate is diluted with 100 ml of water and 50 ml of toluene to give a clear solution. The desired product is now in the basic aqueous phase. The water phase is washed with 150 ml of toluene (3×50 ml). To the water phase is added 75 ml of ethyl acetate. To this reaction mixture 7.1 g (33.66 mmol) of citric acid are added. The protonated product is now in the organic phase. The mixture is allowed to stir at room temperature at the beginning, then later at 50° C. After 12 hours stirring, 3.6 g citric acid (17.1 mmol) are added to the mixture and stirring is continued at 50° C. during 24 h. The water phase is then separated and 7.1 g citric acid in 50 ml of water are added to the organic solution. The biphasic solution is then stirred for additional 6 hours at 50° C. The layers are separated and 7.1 g of citric acid in aqueous solution are added again. The reaction mixture is stirred over night at internal temperature of 50° C. For work up 50 ml of water are added to the reaction solution at room temperature. The organic phase is washed with 50 ml of water (2×25 ml) and 50 ml of NaHCO₃ [8%], (2×25 ml). The organic phase is washed to a neutral pH with 50 ml of water (2×25 ml) and evaporated to yield (VIIIa) as a very viscous oil.

¹H-NMR (400 MHz, DMSO-d₆): (2 rotamers), 7.52-7.50 (d, 1H), 7.37 (s, 1H), 7.04-7.02 (d, 1H), 6.99 (s, 1H), 4.35-4.31 (m, 1H), 4.06-4.04 (t, 2H), 3.83 (s, 3H), 3.49-3.46 (m, 3H), 3.25 (s, 3H), 2.51-2.49 (m, 1H), 2.05-1.95 (m, 4H), 1.87-1.80 (m, 2H), 1.63-1.58 (t, 1H), 1.25 (s, 9H), 0.97-0.95 (d, 3H), 0.92-0.91 (d, 3H), 0.86-0.84 (d, 3H), 0.83-0.81 (d, 3H), 0.80-0.78 (d, 3H).

MS: [MH-Boc]H⁺=450

R$_f$=0.45 (heptane: EtOAc=1:1)

5a) Purification of Compound (VIIIa) Via Salt Formation to Give Crystalline Li-Salt (VIIIa')

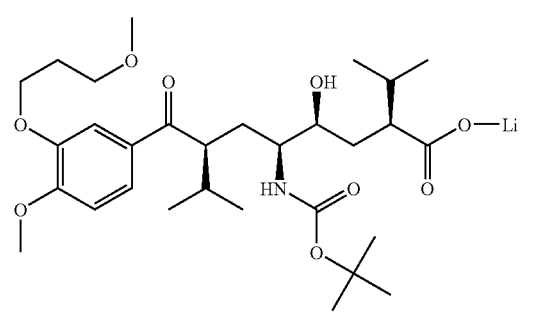

30 g (55 mmol) of crude compound (VIIIa) are dissolved in 120 ml of ethanol to give a clear solution. The solution is cooled to 0° C. and 110 mmol LiOH (2.65 g in 100 ml water) is slowly added under stirring during 45 minutes. The reaction is slightly exotherm. After 2 hours a HPLC control shows complete conversion of starting material to the hydroxyl acid Li compound (VIIIa'). The slightly yellow, turbid solution is partially evaporated by distillation of ca. 100 ml of ethanol-water mixture. The residual concentrated water solution of the Li-salt is extracted twice with ethyl acetate (2×100 ml). The combined ethyl acetate phases which now contain the Li salt (XII) is back extracted with 50 ml saturated sodium chloride solution. The organic phase is then evaporated in vacuum to give 33.0 g of a foam which is dissolved in 30 ml of diisopropylether. To this solution is added at 0° C. 60 ml of n-heptane (isomer mix.). The mixture is seeded and put in the refrigerator over night. The formed crystalline material is filtered and washed with 2 portions (2×30 ml) of cold n-heptane and dried in the vacuum oven over night to obtain a white, crystalline powder.

m.p.: 62-70° C. (melting range)

MS: [M-Li]=566; Li-salt: MH⁺: 574

$^1$H-NMR (600 MHz, DMSO-$d_6$): at room temp. rotamer mix (ca. 1:3): 7.58 (d, min.), 7.5 (d, maj.), 7.43 (br.s, min.), 7.38 (br.s., maj.), 7.05 (d, min.), 6.98 (d, maj.), 6.1 (br.d, —OH, min. +maj.), 4.03 (br.m., —OCH$_2$), 3.82 (s, —OCH$_3$), 3.5-3.35 (br.m., —OCH$_2$, +H$_2$O), 3.22 (s, —OCH$_3$), 3.05 (br.m, 1H), 2.0-1.9 (br.m, 3H), 1.85-1.7 (br.m, 3H), 1.65-1.55 (br.m, 1H), 1.4-1.3 (br.m, 4H), 1.28 (Boc, maj.), 0.95 (Boc, min.), 0.85-0.72 (m, 12H+heptane). at 300° Kelvin: 7.52 (br.d, 1H), 7.45 (br.d, 1H), 7.0 (2d, 1H)

IR: 3350 (br, NH, OH), 2960, 2932, 2873 (s, as CH$_n$), 1686 (C=O), 1581 (as —COO⁻), 1515 (amide, arom.), 1428 (sy. COO⁻), 1267 (C—O), 1174 (C—O-Boc), [cm$^{-1}$].

5b) Reaction of Boc-Lactam-Lactone (VIa) Via Aryl-Alkyl-Mg-Species (VIIb) to Compound (VIIIa)

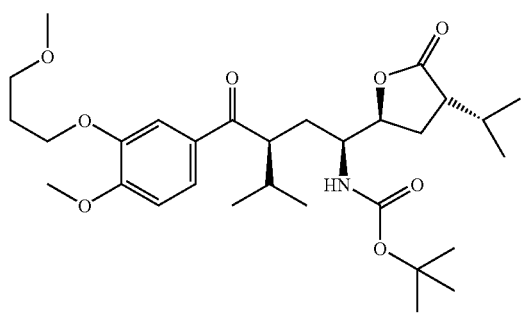

(VIIIa)

A dry flask, (No. 1, 100 ml) is charged with 15 ml of dried THF which is then cooled to 0° C. under argon. When the temperature reached 0° C., 6.25 ml of an isopropyl magnesium chloride solution (2.0 molar, in THF=12.5 mmol) is added. Then 7.5 ml of a n-butyl lithium solution (1.6 molar in n-hexane=12.5 mmol) are added via syringe during 10 minutes. The reaction mixture is stirred at 20-25° C. for 30 minutes. After that time a solution of compound (VII'), X=Br, 2.75 g (10 mmol) in 7.5 ml of dry THF is dropped to the reaction mixture during 15 min. at 25° C., which is slightly exotherm with gas evolution. The dropping funnel is rinsed with 2 ml of THF and the reaction mixture is then stirred at 25° C. for at least 3 hours, followed by a HPLC analysis to check the conversion of VII'.—In a second flask (No. 2) 3.53 g (10 mmol) of compound (VIa) is charged together with 22.5 ml of dry THF under argon. The solution is then cooled to −10° C. To the suspension of (VIa) in flask No. 2 is added the aryl alkyl species (VIIb) via a Teflon tube during a time periode of 1-2 hours under argon pressure. The reaction mixture is then stirred at −10° C. for additional 15 hours.

After HPLC analysis showed complete conversion of (VIa) the reaction mixture is quenched onto a solvent mixture of 25 ml of tBME and 22 ml of water containing 3.2 ml of acetic acid under vigorous stirring at 0° C. during 30 min. Then the aqueous phase is separated and the organic phase is extracted three times with 15 ml of water (total 45 ml). The organic phase is then evaporated in vacuum to an oily residue. The residue is again dissolved in 35 ml of ethanol and treated at 0° C. with an aqueous solution of 0.48 g of lithium hydroxide in 20 ml of water under stirring for 5 hours to give the lithium salt (VIIIa'). The reaction mixture is then concentrated in vacuum to remove most of the ethanol and is then diluted with 35 ml of water and 20 ml of TBME and is stirred for 5 minutes. The organic phase is separated and the aqueous phase is again extracted with 20 ml of TBME. The combined organic phases contain the unwanted lipophilic aromatic side products, while the aqueous phase contains the desired lithium salt (VIIIa'). The basic aqueous phase is neutralized by addition of 5.3 g of solid citric acid under stirring followed by the addition of 40 ml of ethyl acetate. The neutralized aqueous phase is separated and replaced by 3.2 g of additional citric acid dissolved in 30 ml of water. The reaction mixture is then vigorously stirred for 2 hours at 65° C. to achieve lactonisation. After HPLC control shows complete lactonisation 45 ml of saturated sodium bicarbonate solution is added slowly under stirring. Stirring is stopped and the aqueous phase is removed while the organic phase, which contains the product (VIIIa) is again washed twice with 25 ml of water (total 50 ml). Finally the organic phase is evaporated in vacuum to give a very sticky viscous residue (VIIIa) which is pure according to HPLC analysis.

5c) Reaction of Boc-Lactam-Lactone (VIa) and Aryl-Li-Species (VIIa) Via Compound (VIIIa') to Compound (Xa) by Sodium Borohydride Reduction without Going Via (VIIIa)

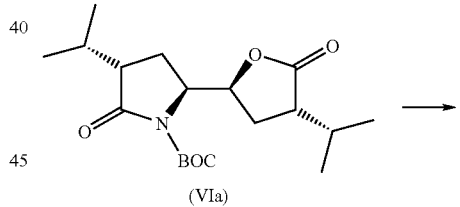

(VIa)

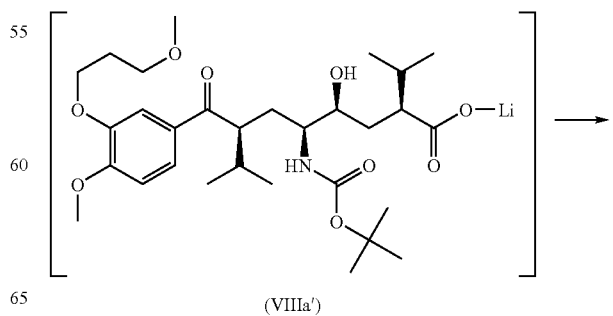

(VIIIa')

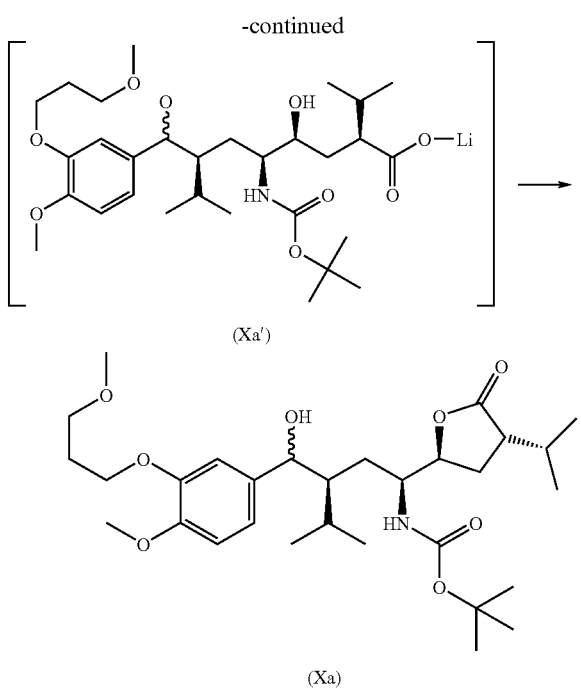

A 750 ml three necked flask was dried under argon flow by heating to 150° C. After cooling down under argon to room temperature the flask is charged with 25 g of bromide (90.8 mmol). The solid is then dissolved by adding 440 ml of dry (mol sieve) tetrahydrofurane. This solution is then cooled down to −78° C. At this temperature a solution of n-butyl-lithium (1.6 molar) in n-hexane (57 ml) is added slowly over 30 minutes to give a clear, colourless solution. The reaction mixture is kept at this temperature vor 1 hour. After that time a HPLC control showed complete halogen-metalation exchange together with ca. 10-15% of homo coupling product.

In a second flask 26.73 g (75.6 mmol) of Boc-compound (VIa) dissolved in 440 ml of dry THF (over mol sieve) is cooled down to −70° C. To this solution is added under argon pressure the Li-species (VIIa) from flask 1 within 15 minutes to give an almost colourless clear solution. After 20 minutes an HPLC control showed complete conversion of (VIa). The reaction mixture is quenched onto a biphasic mixture of 600 ml aqueous citric acid solution (10%) and 500 ml of TBME at 0° C. under vigorous stirring.

The aqueous phase is extracted with 250 ml of TBME. The combined organic phases twice with (2×200 ml) aqueous citric acid, then twice (2×200 ml) sodium bicarbonate (10%) and finally with 2×200 ml of water. The organic phase is dried over $MgSO_4$ and evaporated in vacuum to give a thick oil.

Then this oil (48.6 g) is dissolved in 500 ml of ethanol to give a colourless solution. To this solution is added at 0° C. 151 ml of a 1 molar solution of lithium hydroxide (0.151 mol) under stirring. The reaction mixture is slowly warmed up to room temperature and after 2 hours lactone ring opening was complete (HPLC) to give the lithium salt (VIIIa').

To this solution are added at 40° C. small portions of sodium borohydride are added (3.8 g, 100 mmol) over a period of 2 hours. HPLC control showed after 5 hours 66% conversion of starting material. Additional 756 mg, (20 mmol) of $NaBH_4$ is added and stirring at 40° C. is continued over night. A HPLC analysis showed complete conversion to the epimeric mixture of (Xa'). The reaction mixture was cooled to 0° C. and excess of borohydride was destroyed by slowly adding 400 ml of aqueous citric acid solution (~10%) at 0° C. under stirring to get pH 3. Strong hydrogen gas evolution is observed. The reaction mixture is concentrated in vacuum to remove ethanol. The aqueous phase is extracted with ethyl acetate and the ethylacetate phase is again mixed with 300 ml of an aqueous solution of citric acid and then warmed up to 50-60° C. for 12 hours whereby lactonisation takes place to give the 2 epimeric alcohols (Xa) after phase separation and evaporation as a thick oil which was crystallized from TBME/heptane mixture to give a white crystalline solid in the ratio of 95:5. Spectroscopic data are in accordance with (Xa) epimeric mixtures.

6) Preparation of Compound (IX), (Penultimate Precursor) by Direct Hydrogenation of Compound (VIIIa)

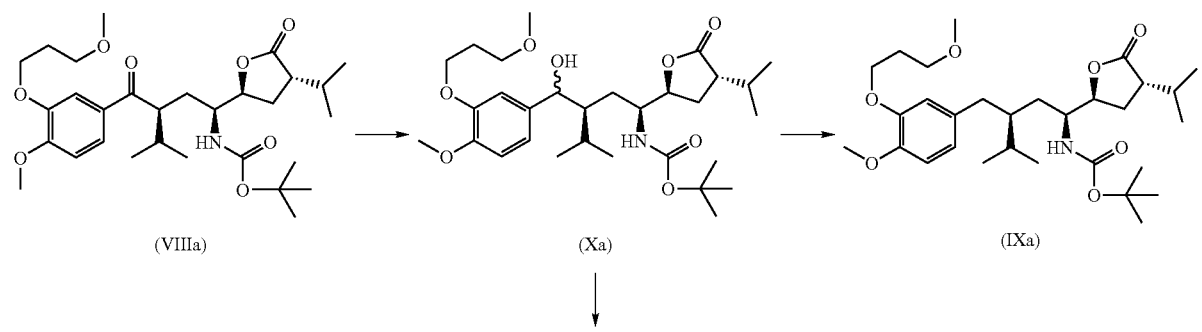

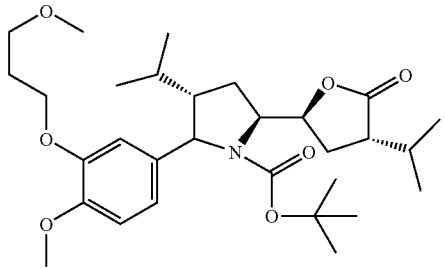

(XIa)

2.75 g (5 mmol) of compound (VIIIa) are dissolved in 30 ml of a mixture of ethanol:acetic acid (2:1) and 0.35 g of catalyst Pd—C (10%), Engelhard 4505 is added. The hydrogenation is performed at 50° C. and 5 bar pressure. After 10 h a sample shows uncomplete conversion. An additional amount of catalyst (0.35 g) is added and hydrogenation is continued. After 46 hours almost all starting material is converted. The reaction mixture is filtered and washed with ethanol and the filtrate is evaporated in vacuum to give an almost colourless oil. The crude product mixture was dissolved in toluene and was washed 3-times with 25 ml of saturated NaHCO$_3$-solution to neutralize the acetic acid and extract it to the aqueous phase. After evaporation of the toluene in vacuum an almost colourless viscous oil was obtained (2.21 g). The tlc (SiO$_2$, heptane:ethyl acetate (1:1) of this mixture showed 4 different spots besides small amounts of starting material (VIII, R$_f$ 0.45) which were visualized by spraying with Dragendorf's reagent. The spot on the top with R$_f$=0.60 was the desired compound (IXa). The two spots with R$_f$ 0.33 and 0.40 are the 2 different epimers of the alcohol derivative (Xa). The spot with R$_f$ 0.55 is compound (XI) which is formed from epimeric compounds (Xa) with R$_f$ 0.33 and 0.40 under acidic conditions (AcOH) at higher temperature or with ion exchange resin at room temperature. Similar behaviours could be observed in HPLC.

After preparative column chromatography of the 2.21 g of the crude mixture 20 pure fractions of the desired compound (IXa), R$_f$=0.60, could be collected which crystallized directly from the oil. The crystalline material was recrystallized from heptane.

Compound (IXa):
 M.p: 78-79° C.

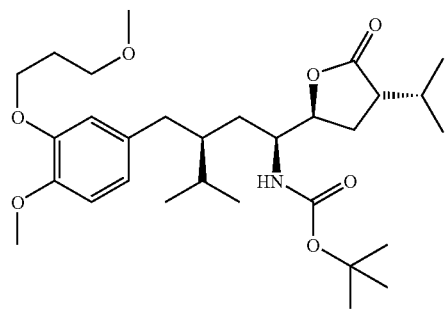

$^1$H-NMR (400 MHz, CDCl$_3$): 0.74-0.76 (2×d, 6H), 0.85-0.87 (d, 3H), 0.92-0.94 (d, 3H), 1.16-1.23 (bm, 1H), 1.38, (s, 9H, Boc), 1.5-1.65 (br-m, 2H), 1.95-2.15 (br-m, 5H), 2.50-2.35 (br-m, 1H), 2.45-2.52 (brm, 1H), 2.50-2.59 (brm, 1H), 3.28 (s, 3H), 3.50 (t, 2H), 3.70-3.80 (s+m, 4H), 4.03 (t, 2H), 4.28-4.35 (m, 2H), 6.62 (d, 1H), 6.67 (s, 1H), 6.69 (d, 1H).

IR: 3358 (—NH), 1773 (lacton), 1705 (carbamat), 1518 (amide II) cm$^{-1}$;

(FTIR-microskop in transmission)

MS: MH$^+$=535.7

Also the other "spots" are isolated and characterized by spectroscopic data:

Spot at R$_f$=0.55 Corresponds to Compound (XIa)

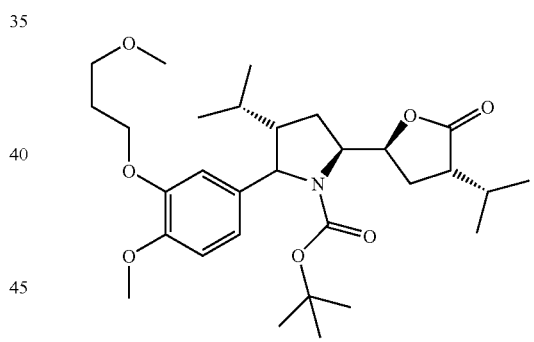

$^1$H-NMR (400 MHz, CDCl$_3$): 0.77-0.79 (d, 3H), 0.86-0.88 (d, 3H), 0.88-0.90 (d, 3H), 0.97-0.99 (d, 3H), 1.10-1.30 (br-peak, 9H, boc), 1.78-1.86 (m, 1H), 2.0-2.06 (m, 2H), 2.08-2.16 (brm, 3H), 2.50-2.60 (brm, 1H), 3.27 (s, 3H), 3.50 (t, 2H), 3.77 (s, 3H), 4.0-4.10 (brm, 3H), 4.20-4.40 (br-peak, 2H), 6.72-6.74 (d, 1H), 6.75-6.77 (d, 1H), 6.83 (s, 1H).

m.p.: 63-69° C.

IR: 3057, 2970, 1773 (lacton), 1688 (Boc), 1515, 1390, 1368 [cm−1]

MS: MH$^+$=534; M-NH$_4$$^+$=551

Spot at R$_f$=0.40 Corresponds to Compound (Xa)-Epimer 1 (Syn-Epimer According to X-Ray Structure Analysis:

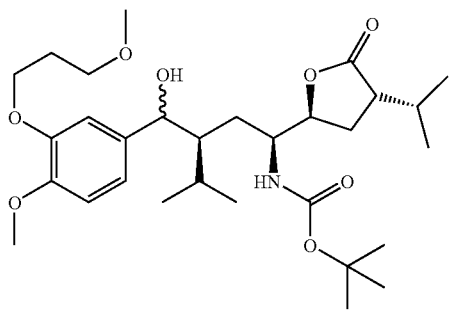

(Xa)

$^1$H-NMR (400 MHz, CDCl$_3$): 0.82-0.88 (3×d, 9H), 0.92-0.94 (d, 3H), 1.40 (s, 9H), 1.80-1.93 (brm, 2H), 2.03-2.11 (brm, 4H), 2.37-2.45 (brm, 1H), 3.32 (s, 3H), 3.35 (t, 2H), 3.83 (s, 3H), 4.05-4.20 (brm, 3H), 4.25 (d, 1H), 4.60 (d, 1H), 6.80 (d, 1H), 4.83 (dd, 1H), 6.95 (s, 1H).

MS: M+NH$_4$$^+$=569; M−H=550

7) Preparation of Compound (IXa), by Direct Hydrogenation of Compound (VIIIa) in EtOH H$_2$O (9:1) at Normal Pressure & Room Temperature with Pd—C, 10%, Wet, JM-Type39:

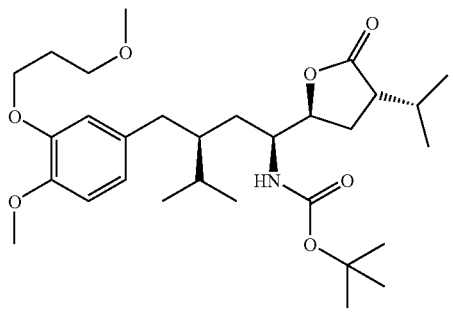

(IXa)

5.5 g (10 mmol) of compound (VIIIa) was dissolved in of a mixture of 90 ml ethanol and 10 ml water. To the mixture is added 5 g of catalyst Pd—C (10%), water cont. ca. 50%, from Johnson Matthey, typ 39. The mixture is stirred at room temperature and normal pressure for 20 hours. After that time the conversion of compound (VIIIa) was 98% and 66% of the desired compound (IXa) was formed together with 28% of epimeric alcohols (Xa) and 4% pyrrolidine lactone (XIa). Hydrogenation under the same conditions was continued for another 48 hours without additional catalyst. After that time the catalyst was filtered off and the solvent was evaporated under reduced pressure to afford an oil (5.9 g) which contained according to HPLC 89% of compound (IXa) and each 5% compound (XIa) and starting material (VIIIa). The oil was treated and stirred at 0° C. with 10 ml of n-heptane (isomer mix) and seeded with a small amount of compound (IXa) upon the product started to crystallize. The flask was stored in the refrigerator over night and for another 24 hours at −18° C. The product was filtered and washed with small volumes of very cold n-heptane to give after drying in vacuum the desired product, which was pure by HPLC, TLC and 1H-NMR.

8) Preparation of Compound (Xa), (Syn-Anti Epimeric Alcohols) by Hydrogenation of Compound (VIIIa) in EtOAc at 6 Bar, 20-60° C. with Catalyst Pd—C, 10%, in the Presence of Potassium Formate

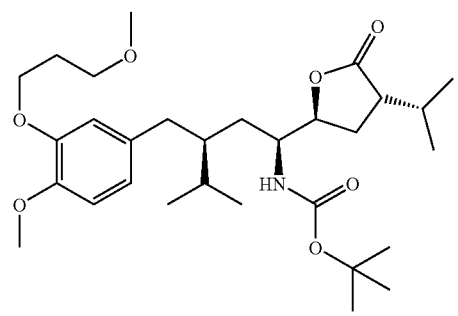

(IXa)

22.0 g (40 mmol) of compound (VIIIa) as an oil are dissolved in 150 ml of ethyl acetate. 10 g of Pd/C (10%), type Engelhard 4505, and 500 mg of potassium formate was added to buffer acidic components of the catalyst. Hydrogenation was performed with 6 bar and room temperature at the beginning and was later increased to 60° C. After 8 days additional catalyst (5 g) was added and after 9 days the conversion was 91% and the 2 epimeric alcohols were formed in a ratio of 93:7 (syn:anti) exclusively without any further hydrogenolysis to compound (IXa) or formation of compound (XIa). The catalyst was filtered off and the solvent was evaporated in vacuum to give an oil which crystallized during standing at room temperature (19.0 g). This material was re-crystallized from tert.-butyl methylether (20 ml) and n-heptane (60 ml, iso mixture) at 20° C. and seeding. After crystallization is almost complete (2 h) additional 40 ml of n-heptane is added at 20° C. under stirring for 2 hours to give then after storage in the refrigerator over night and filtration, washing with cold n-heptane and drying the white crystalline material (syn/anti ratio=93:7, HPLC).

m.p. of the syn/anti alcohol mixture: 69-71° C.

8) Preparation of Compound (Xa'), (Salt of Hydroxy Acid from Syn-Anti Epimeric Alcohol (Xa)

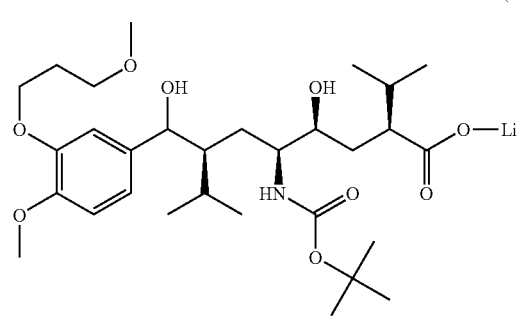

(Xa')

1 g (1.8 mmol) of an epimeric mixture of crystalline alcohols (Xa), (ratio ca. 9:1) is dissolved in 10 ml of ethanol. The solution is cooled to 0° C. and a solution of lithium hydroxide (3.6 mmol) in water (4 ml) is added under stirring. After stirring at ambient temperature for 2 hours the reaction is complete. Most of the ethanol is removed by distillation and the residual aqueous phase is extracted with 2×20 ml of ethyl acetate. The combined ethyl acetate extracts are washed with 5 ml of brine and is then evaporated to an oily solid. To this is added 5 ml of n-heptane to crystallize the material. The crystalline suspension is stored over night in the refrigerator and is then filtered and washed with cold n-heptane and dried in vacuum to give a white solid.

m.p.: 118-128° C. (melting range)

MS: [M-Li]$^-$=568; MH$^+$=576

IR: FTIR microscope i. transmission: 3440, 3355, 3167 (br, NH, OH); 2958, 2874(aliph.-CH), 1686 (C=O,Boc), 1605 (as, COO), 1555(amide-II), 1514, 1438 (sy, COO$^-$), 1367, 1258, 1171, 1028, [cm$^{-1}$]

9) Preparation of Compound (IXa'), Li-Salt of Hydroxy Acid from (IXa)

10) Hydrogenation of Compound (VIIIa'), (Salt of Hydroxy Acid from (VIIIa)) with Pd—C to Compound (Xa') as Epimeric Mixture

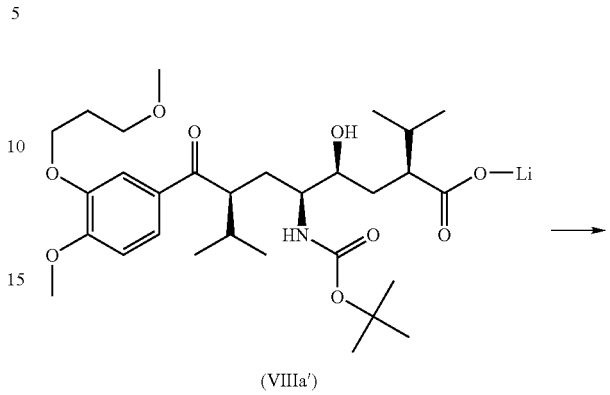

(VIIIa')

1 g (1.86 mmol) of crystalline compound (IXa) was dissolved in 10 ml of ethanol. To this solution was added a solution of 88.6 mg (3.7 mmol) of lithium hydroxide in 5 ml of water. The homogeneous reaction mixture was stirred at room temperature for 2 hours. HPLC showed after that time complete conversion. The solution was evaporated in vacuum to remove most of the ethanol. The aqueous phase was extracted with 2×20 ml of ethyl acetate. The combined ethyl acetate phases are washed with 5 ml of brine and are then evaporated to give a sticky solid. To this is added 10 ml of n-heptane under stirring at 0° C. to crystallize the material. The crystalline suspension is stored over night in the refrigerator and is then filtered and washed with cold n-heptane and dried in vacuum to give a white solid.

m.p.: 88-98° C. (melting range)

IR: FTIR-microscope in transmission: 3573(—OH), 3377 (—NH), 2955, 2933, 2871, 1679(Boc), 1572(COO$^-$), 1514 (amide-II), 1439, 1423(COO$^-$), 1366, 1260, 1239, 1170, 1122, 1026 [cm$^{-1}$]

MS: [M-Li]$^-$=552; MH$^+$=560

2.8 g of (5.0 mmol) of carboxy-Li-salt (compound VIIIa') was dissolved in 40 ml of isopropanol. 2.5 g of Pd—C (10%), JM type 39, wet, was added and hydrogenated at 25° C. over night (17 h) at 0.2 bar. After that time conversion of compound (VIIIa') was 86% (HPLC). Temperature was increased to 50° C. and hydrogenation was continued for additional 24 hours. After 41 hours only small changes in conversion were observed but the ratio of syn/anti epimeric alcohols has changed from 83% syn/17% anti to 67% syn/33% anti. Therefor additional catalyst (1 g) was added and hydrogenation was continued at 50° C. for additional 6 hours. After that time HPLC analysis showed no further conversion but again a change in the syn/anti ration to 62:38. Hydrogenation was continued at 50° C. for additional 36 hours without additional catalyst loading. After that time HPLC analysis showed a syn/anti ratio of 45:55, but no further change in conversion (83%) of starting material. This shows an interconversion of the syn epimeric alcohol to the anti epimer under the reaction conditions by an oxidative-reductive cycle. Hydrogenation was stopped, the catalyst was filtered off and the solvent was evaporated to a semi-solid oil.

11) Reduction of Li-Salt (VIIIa') with Sodium Borohydride Via (Xa)' to (Xa) Using Sodium Borohydride Reduction in Ethanol-Water (1:1):

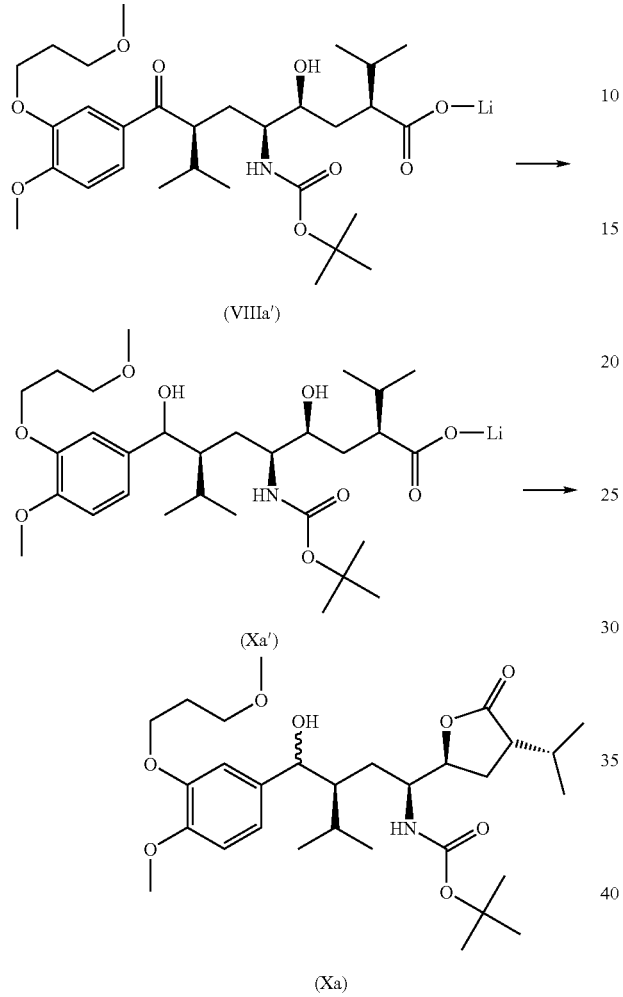

(VIIIa')

(Xa')

(Xa)

2.3 g (4 mmol) of Li-salt (VIIIa') is dissolved at room temperature in a mixture of 10 ml of water and 10 ml of ethanol. The solution is warmed up to 40° C. and small portions of sodium borohydride are added (151 mg, 4 mmol) over a period of 1 hour. HPLC control showed after 4 hours 66% conversion of starting material. Additional 38 mg, (1 mmol) of $NaBH_4$ is added and stirring at 40° C. is continued over night. HPLC analysis showed complete conversion. Excess of borohydride was destroyed by quenching on 40 ml of aqueous citric acid solution (10%) to get pH 3. The reaction mixture is concentrated in vacuum to remove ethanol. The aqueous phase is extracted with ethyl acetate and the ethylacetate phase is again mixed with 10 ml of an aqueous solution of citric acid and then warmed up to 50-60° C. for 2 hours whereas lactonisation takes place to give the 2 epimeric alcohols (Xa) after phase separation and evaporation as a an sticky oil which crystallized from TBME/heptane as a white solid in the ratio of 95:5. HPLC and spectroscopic data are in accordance with other samples of (Xa) mixtures.

Other solvent mixtures like THF/water, or i-propanol/water or water alone or ethanol with 20 vol. % of water are also good solvents for this borohydride reduction.

12) Barton-McCombie-Route to Compound (IXa)

a) Preparation of compound (XVa)=Imidazole-1-carbothioic acid O-{(S)-2-[(S)-2-tert-butoxycarbonylamino-2-((2S,4S)-4-isopropyl-5-oxo-tetrahydro-furan-2-yl)-ethynl]-1-[4-methoxy-3-(3-methoxy-propoxy)-phenyl]-3-methyl-butyl}ester

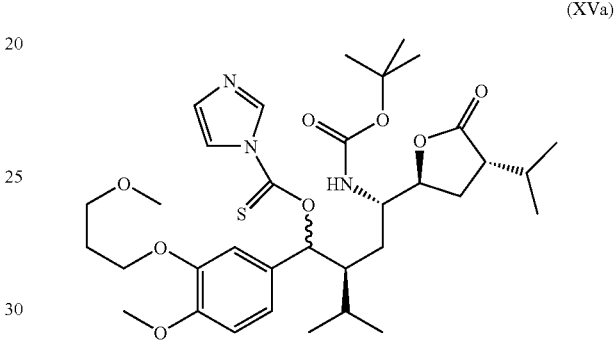

(XVa)

Epimeric compound (Xa) (1.66 g, 3 mmole) is dissolved in toluene (18 mL) and 1,1-thiocarbonyl-diimidazole (0.804 g, 4.5 mmole) is added, followed by the addition of dimethylaminopyridine (0.037 g). The reaction mixture is stirred over night at room temperature. For work-up, aqueous, saturated NaHCO3 (20 mL) is added and the layers are separated. The organic layer is extracted with aq., sat. NaHCO3 (20 mL) and with water (20 mL). The organic layer is dried on anhydrous MgSO4 and the solvent is evaporated under reduced pressure to obtain 2.08 g crude product as a viscous liquid. The crude product was purified by flash-chromatography on silica gel with t-butyl-methyl ether as mobile phase to obtain pure compound (XVa) as a white foam. 1H-NMR, IR and HR-MS Spectra of the product confirmed the proposed structure as a mixture of diastereoisomers (epimers). The $^1$H-NMR spectrum was complicated by the presence of rotamers. $^1$H-NMR (400 MHz, 354K, $d_6$-DMSO): 0.65-0.99 (m, 12H), 1.42 (s, 9H), 1.44-2.44 (m, 10H), 3.24 (s, 3H), 3.47 (t, 2H), 3.75 (s, 3H), 3.76-3.90 (m, 1H), 4.01 (t, 2H), 4.06-4.40 (m, 1H), 4.73-4.89 (m, 1H), 6.81-7.03 (m, 3H), 7.05 (broad s, 1H), 7.62 (broad s, 1H), 8.28 (broad s, 1H). FT-IR (in transmission): 3317, 3125, 2961, 2933, 2875, 2836, 1769, 1701, 1604, 1591, 1517, 1469, 1427, 1390, 1366, 1331, 1290, 1265, 1221, 1168, 1143, 1120, 1097, 1064, 1046, 1026, 968, 949, 886, 811, 753, 725, 694, 666, 646 cm$^{-1}$. HR-MS: $C_{34}H_{51}N_3O_8S$. Calculated for MNa$^+$=684.32891 found: 684.32894; Calculated for MK$^+$=700.30284, found: 700.30306.

b) Preparation of Compound (IXa) by Reduction of Compound (XVa) with Tributyltin Hydride

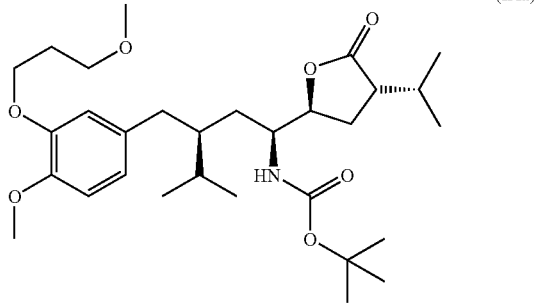
(IXa)

Compound (XVa) (=Imidazole-1-carbothioic acid O-{(S)-2-[(S)-2-tert-butoxycarbonylamino-2-((2S,4S)-4-isopropyl-5-oxo-tetrahydro-furan-2-yl)-ethyl]-1-[4-methoxy-3-(3-methoxy-propoxy)-phenyl]-3-methyl-butyl}ester) (0.4 g, 0.604 mmole) is dissolved in toluene (8 mL). The solution is heated to 100° C. Tributyltin hydride (0.916 g is added via a syringe at this temperature, followed by the addition of a solution of AIBN (0.01984 g) in tetrahydrofuran (0.4 mL). The reaction mixture is stirred for 1 hour at 100° C., after which time another portion of AIBN (0.01984 g) in tetrahydrofuran (0.4 mL) is added. Stirring was continued for one additional hour at 100° C. and the reaction was quenched by addition of the reaction mixture onto cold methanol (10 mL) at −20° C. Toluene (10 mL) is added and the mixture is extracted with aqueous 1N HCl (2×10 mL) and with water (10 mL). The aqueous layers are combined and are extracted with toluene (10 mL). The organic layers are combined, dried on anhydrous $Na_2SO_4$ and the solvent was evaporated under reduced pressure. The oily crude product was purified by flash-chromatography on silica gel with hexane fraction/isopropanol (9:1) to obtain compound (IXa). The product was identical to a reference sample of compound IXa according to HPLC and 1H-NMR.

c) Preparation of Compound (IXa) by Reduction of Compound (XVa) with tris(trimethylsilyl)silane

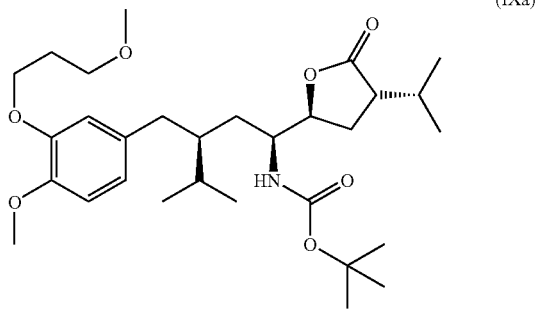
(IXa)

Compound (XVa) (=Imidazole-1-carbothioic acid O-{(S)-2-[(S)-2-tert-butoxycarbonylamino-2-((2S,4S)-4-isopropyl-5-oxo-tetrahydro-furan-2-yl)-ethyl]-1-[4-methoxy-3-(3-methoxy-propoxy)-phenyl]-3-methyl-butyl}ester) (0.4 g, 0.604 mmole) is dissolved in a mixture of toluene (4 mL) and tert-dodecylmercaptane (4 mL). The solution is heated to 100° C.

Tris(trimethylsilyl)silane (774.5 mg, 3 mmole) is added, followed by the addition of a solution of AIBN (20 mg) in toluene (0.4 mL). The reaction mixture is stirred for 15 minutes at 100° C. and is poured onto cold methanol (10 mL) at −20° C. to quench the reaction. Toluene (10 mL) is added and the mixture is extracted with aqueous 1N HCl (2×10 mL) and water with (10 mL). The aqueous layers are combined and extracted with toluene (10 mL). The organic layers are combined, dried over anhydrous sodium sulphate and the solvent is evaporated. The crude product was purified by flash chromatography on silica gel to obtain pure compound 4 (30 mg, 18.5% yield). The product was identical to a reference sample of compound IXa according to HPLC and $^1$H-NMR.

13) Synthesis of Bis-Pseudoephedrine Precursor (Ia'vi) from (+)-(1S,2S)-Pseudoephedrine as Auxiliary: According to Lit: A. Myers et al., J.A.C.S., 119, 6496 (1997)

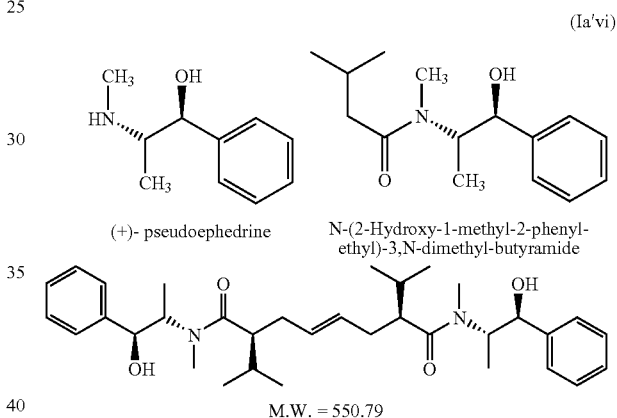
(Ia'vi)

M.W. = 550.79

A 100 ml three necked flask was dried under argon flow by heating to 150° C. After cooling down under argon to room temperature, 2.54 g (60 mmol) of dried lithium chloride was added. Then 3.15 ml of diisopropylamine dissolved in 12 ml of dry THF is added under stirring. The resulting suspension is cooled to −78° C. under argon. To this suspension is added under stirring at −78° C. via syringe 13 ml of a 1.6 molar solution of butyl lithium in hexane to give LDA. After stirring the suspension for further 15 minutes, a solution of 2.5 g of N-isovaleroyl-(S,S)-pseudo-ephedrine (10 mmol) dissolved in 10 ml of THF is added via syringe at −78° C. Then the suspension is warmed up to 0° C. within 30 min. At this temperature a solution of 1.18 g (5.5 mmol) of trans-1,4-dibromo-2-butene in 5 ml of THF is added via syringe. Stirring is continued at 0-5° C. for further 30 min. After stirring the reaction mixture at room temperature over night a HPLC control showed complete conversion. The reaction mixture is quenched onto a mixture of 80 ml of aqueous ammonium chloride solution and 50 ml of TBME. The aqueous phase is extracted twice with 25 ml of TBME. Then the combined organic phases are washed with brine (50 ml) dried over $MgSO_4$ and are finally filtered and evaporated in vacuum to give a very viscous oil which results in a white foam after evacuation in high vacuum. MS, $^1$H-NMR in $d_6$-DMSO at room temperature (300° K) and at elevated temperature (394°

K) confirm the structure. The compound exists at RT as a mixture of 2 rotamers in the ratio (~2:1).

MS: 551 (MH+)

IR: 3350 (br, OH), 2960, 1608(amid), 1450, 1407, 1030, 970, 755, 700 [cm$^{-1}$]

$^1$H-NMR, 600 MHz (d$_6$-DMSO): complex spectrum, 2 sets of signals, at 300° K (mixture of rotamers ~2:1).

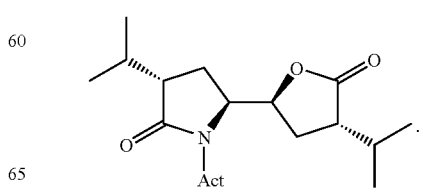

16. The compound according to claim 14, having the formula
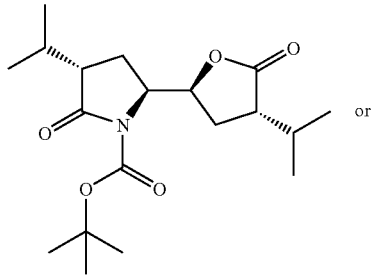 or 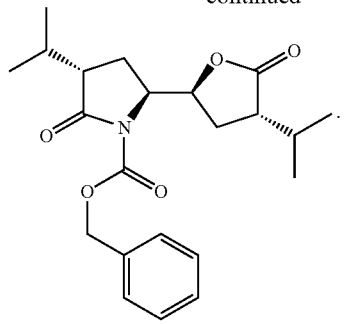

What is claimed is:

1. A compound of the formula (II)

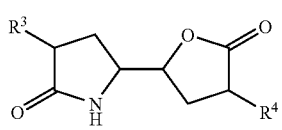

wherein
R$^3$ is C$_{1-7}$alkyl or C$_{3-8}$cycloalkyl; and
R$^4$ is C$_{1-7}$alkyl, C$_{2-7}$alkenyl, C$_{3-8}$cycloalkyl, phenyl- or naphthyl-C$_{1-4}$alkyl each unsubstituted or mono-, di- or tri-substituted by C$_{1-4}$alkyl, O—C$_{1-4}$alkyl, OH, C$_{1-4}$alkylamino, di-C$_{1-4}$alkylamino, halogen and by trifluoromethyl;
or a salt thereof.

2. The compound according to claim 1 wherein R$^3$ and R$^4$ are independently branched C$_{3-6}$alkyl.

3. The compound according to claim 1 having the following stereochemistry:

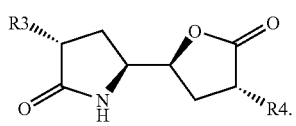

4. The compound according to claim 1, having the formula

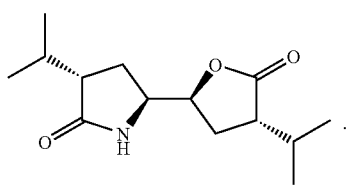

5. A compound of the formula (II')

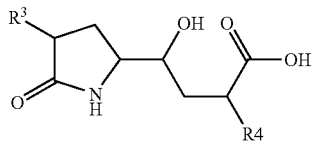

wherein
R$^3$ is C$_{1-7}$alkyl or C$_{3-8}$cycloalkyl; and
R$^4$ is C$_{1-7}$alkyl, C$_{2-7}$alkenyl, C$_{3-8}$cycloalkyl, phenyl- or naphthyl-C$_{1-4}$alkyl each unsubstituted or mono-, di- or tri-substituted by C$_{1-4}$alkyl, O—C$_{1-4}$alkyl, OH, C$_{1-4}$alkylamino, di-C$_{1-4}$alkylamino, halogen and by trifluoromethyl;
or a salt thereof.

6. The compound according to claim 5 wherein R$^3$ and R$^4$ are independently branched C$_{3-6}$alkyl.

7. The compound according to claim 5 having the following stereochemistry:

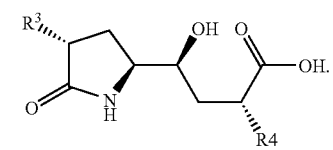

8. The compound according to claim 5, having the formula

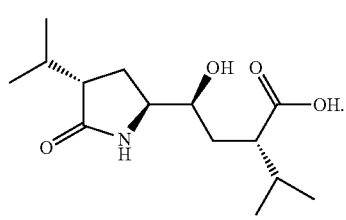

9. A method for preparing a compound of formula (II) according to claim 1, said method comprising subjecting a compound of formula (I')

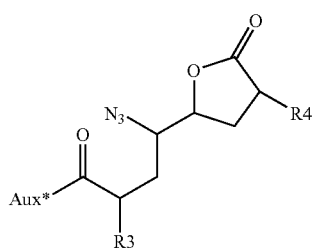

wherein R$^3$ and R$^4$ are as defined for a compound of formula (II) and Aux* is an auxiliary able to form an ester or amide with the carbonyl functionality, or a salt thereof, to hydrogenation to convert the azide moiety to an amine and to effect lactam ring closure.

10. A method for preparing a compound of formula (II) according to claim 1, said method comprising subjecting a compound of formula (I)

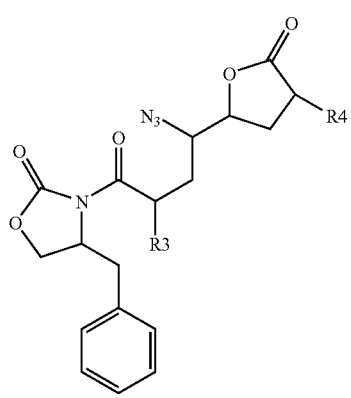

wherein R³ and R⁴ are as defined for a compound of formula (II), or a salt thereof, to hydrogenation to convert the azide moiety to an amine and to effect lactam ring closure.

11. A method for preparing a compound of formula (II) according to claim 1, said process comprising subjecting a compound of formula (III)

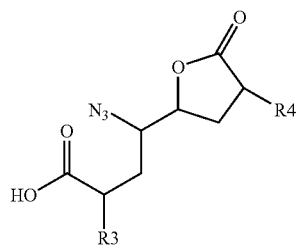
(III)

wherein R³ and R⁴ are as defined for a compound of formula (II), or a salt thereof, to conversion to an anhydride of formula (IV)

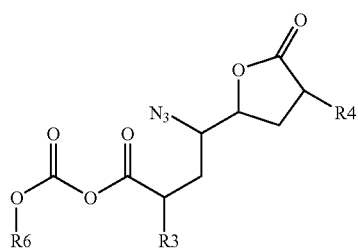
(IV)

wherein R³ and R⁴ are as defined for a compound of formula (II) and R⁶ is C₁₋₇alkyl or C₃₋₈cycloalkyl, or a salt thereof; to activate the acid moiety followed by hydrogenation to convert the azide moiety to an amine and to effect lactam ring closure.

12. A method for preparing a compound of formula (II) according to claim 1, said process comprising subjecting a compound of formula (III)

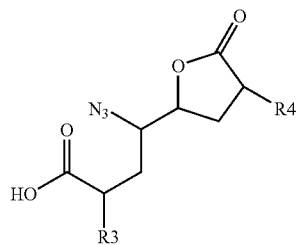
(III)

wherein R³ and R⁴ are as defined for a compound of formula (II), or a salt thereof, to conversion to an ester of formula (V)

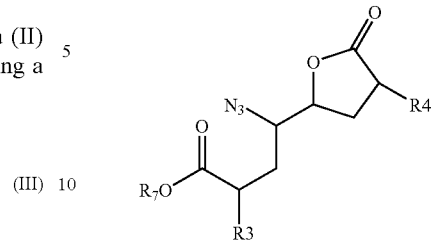
(V)

wherein R³ and R⁴ are as defined for a compound of formula (II) and R⁷ is C₁₋₇alkyl or C₃₋₈cycloalkyl, or a salt thereof; followed by hydrogenation to convert the azide moiety to an amine and to effect lactam ring closure.

13. A method for preparing a compound of formula (VI)

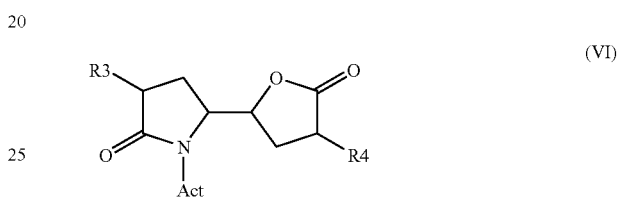
(VI)

wherein R³ and R⁴ are as defined for a compound of formula (II) and Act is an activating group selected from an amino protecting group, in particular a carbamate, or a salt thereof; comprising introducing the activating group at the nitrogen of a compound of formula (II) as given in claim 1, or a salt thereof.

14. A compound of formula (VI)

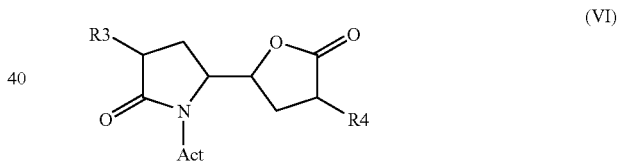
(VI)

wherein
R³ is C₁₋₇alkyl or C₃₋₈cycloalkyl;
R⁴ is C₁₋₇alkyl, C₂₋₇alkenyl, C₃₋₈cycloalkyl, phenyl or naphthyl-C₁₋₄alkyl each unsubstituted or mono-, di- or tri-substituted by C₁₋₄alkyl, O—C₁₋₄alkyl, OH, C₁₋₄alkylamino, di-C₁₋₄alkylamino, halogen and by trifluoromethyl; and
Act is an activating group selected from an amino protecting group, in particular a carbamate;
or a salt thereof.

15. The compound according to claim 14, having the formula